US008409839B2

(12) United States Patent
Koch et al.

(10) Patent No.: US 8,409,839 B2
(45) Date of Patent: Apr. 2, 2013

(54) POLYPEPTIDES HAVING CELLOBIOHYDROLASE II ACTIVITY

(75) Inventors: Nadine Koch, Cologne (DE); Oliver Kensch, Cologne (DE); Klaus Schulze-Pellengahr, Cologne (DE)

(73) Assignee: Direvo Industrial Biotechnology GmbH, Cologne (DE)

( * ) Notice: Subject to any disclaimer, the term of this patent is extended or adjusted under 35 U.S.C. 154(b) by 0 days.

(21) Appl. No.: 13/133,872

(22) PCT Filed: Dec. 9, 2009

(86) PCT No.: PCT/EP2009/008792

§ 371 (c)(1), (2), (4) Date: Aug. 26, 2011

(87) PCT Pub. No.: WO2010/066411

PCT Pub. Date: Jun. 17, 2010

(65) Prior Publication Data

US 2011/0300263 A1 Dec. 8, 2011

Related U.S. Application Data

(60) Provisional application No. 61/121,366, filed on Dec. 10, 2008.

(51) Int. Cl.

| | |
|---|---|
| *C12N 9/24* | (2006.01) |
| *C12N 1/00* | (2006.01) |
| *C12P 1/00* | (2006.01) |
| *C07H 21/04* | (2006.01) |

(52) U.S. Cl. .................. 435/200; 435/209; 435/252.33; 435/254.11; 435/320.1; 435/41; 536/23.2

(58) Field of Classification Search ........................ None
See application file for complete search history.

(56) References Cited

U.S. PATENT DOCUMENTS 7,348,168 B2 * 3/2008 Wu et al. ........................ 435/161

FOREIGN PATENT DOCUMENTS

| | | |
|---|---|---|
| WO | WO 02/30953 | 4/2002 |
| WO | WO 2006/074005 | 7/2006 |
| WO | WO 2008/137958 | 11/2008 |

* cited by examiner

*Primary Examiner* — Nashaat Nashed

(74) *Attorney, Agent, or Firm* — Fanelli Haag & Kilger PLLC

(57) ABSTRACT

Provided herein are improved variants of polypeptides having cellobiohydrolase II activity, nucleic acids encoding the polypeptides, vectors, host cells containing the nucleic acids and methods for producing the polypeptides. The polypeptides encompassed by this disclosure may be used in numerous applications including the use of the polypeptides for the production of biofuels and for the synthesis of platform chemicals or biopolymers from renewable sources.

20 Claims, 14 Drawing Sheets

FIGURE 2

Amino acid sequence of wild-type Trichoderma reesei CBHII protein (SEQ ID NO: 1)

| | | | | | | |
|---|---|---|---|---|---|---|
| 1 | MIVGILTTLA | TLATLAASVP | LEERQACSSV | WGQCGGQNWS | GPTCCASGST | 50 |
| 51 | CVYSNDYYSQ | CLPGAASSSS | STRAASTTSR | VSPTTSRSSS | ATPPPGSTTT | 100 |
| 101 | RVPPVGSGTA | TYSGNPFVGV | TPWANAYYAS | EVSSLAIPSL | TGAMATAAAA | 150 |
| 151 | VAKVPSFMWL | DTLDKTPLME | QTLADIRTAN | KNGGNYAGQF | VVYDLPDRDC | 200 |
| 201 | AALASNGEYS | IADGGVAKYK | NYIDTIRQIV | VEYSDIRTLL | VIEPDSLANL | 250 |
| 251 | VTNLGTPKCA | NAQSAYLECI | NYAVTQLNLP | NVAMYLDAGH | AGWLGWPANQ | 300 |
| 301 | DPAAQLFANV | YKNASSPRAL | RGLATNVANY | NGWNITSPPS | YTQGNAVYNE | 350 |
| 351 | KLYIHAIGPL | LANHGWSNAF | FITDQGRSGK | QPTGQQQWGD | WCNVIGTGFG | 400 |
| 401 | IRPSANTGDS | LLDSFVWVKP | GGECDGTSDS | SAPRFDSHCA | LPDALQPAPQ | 450 |
| 451 | AGAWFQAYFV | QLLTNANPSF | L | | | 471 |

FIGURE 3

Amino acid sequence of wild-type Trichoderma reesei CBHII protein showing the locations of beneficial mutations at positions Q37, N38, Y53, S54, A65, A66 and H438 (highlighted). (SEQ ID NO: 2)

| | | | | | | |
|---|---|---|---|---|---|---|
| 1 | MIVGILTTLA | TLATLAASVP | LEERQACSSV | WGQCGGQNWS | GPTCCASGST | 50 |
| 51 | CVYSNDYYSQ | CLPGAASSSS | STRAASTTSR | VSPTTSRSSS | ATPPPGSTTT | 100 |
| 101 | RVPPVGSGTA | TYSGNPFVGV | TPWANAYYAS | EVSSLAIPSL | TGAMATAAAA | 150 |
| 151 | VAKVPSFMWL | DTLDKTPLME | QTLADIRTAN | KNGGNYAGQF | VVYDLPDRDC | 200 |
| 201 | AALASNGEYS | IADGGVAKYK | NYIDTIRQIV | VEYSDIRTLL | VIEPDSLANL | 250 |
| 251 | VTNLGTPKCA | NAQSAYLECI | NYAVTQLNLP | NVAMYLDAGH | AGWLGWPANQ | 300 |
| 301 | DPAAQLFANV | YKNASSPRAL | RGLATNVANY | NGWNITSPPS | YTQGNAVYNE | 350 |
| 351 | KLYIHAIGPL | LANHGWSNAF | FITDQGRSGK | QPTGQQQWGD | WCNVIGTGFG | 400 |
| 401 | IRPSANTGDS | LLDSFVWVKP | GGECDGTSDS | SAPRFDSHCA | LPDALQPAPQ | 450 |
| 451 | AGAWFQAYFV | QLLTNANPSF | L | | | 471 |

FIGURE 4

```
Trichoderma reesei                 1 mivgilttlatlatlaasvpleerqacssvwgqcggqnwsgptccasgstcvysndyysqclpgaas ...

Trichoderma koningii               1 mivgilttlatlatlaasvpleerqacssvwgqcggqnwsgptccasgstcvysndyysqclpgaas ...
Hypocrea koningii                  1 mivgilttlatlatlaasvpleerqacssvwgqcggqnwsgptccasgstcvysndyysqclpgaas ...
Trichoderma  parceramosum          1 mivgilttlatlatlaasvpleerqacssvwgqcggqnwsgptccaagstcvysndyysqcppgaas ...
Trichoderma viride                 1 mivgilttlatlatlaasvpleerqacssvwgqcggqnwsgptccasgstcvysndyysqclpgaas ...
Hypocrea jecorina                  1 mivgilttlatlatlaasvpleerqacssvwgqcggqnwsgptccasgstcvysndyysqclpgaas ...
Aspergillus clavatus                   1 mknfapslalslllptvqaqqtmwgqcggagwsgatdcvaggvcstqnayyaqclpgatt ...
Aspergillus fumigatus                  1 mkhlassialtlllpavqaqqtvwgqcggqgwsgptscvagaacstlnpyyaqcipgata ...
Aspergillus nidulans                   1 mhysasglalafllpaiqaqqtlygqcggsgwtgatscvagaacstlnqwyaqclpaatt ...
Aspergillus niger                      1 mhyplsla-laflpfgiqaqqtlwgqcggqgysgatscvagatcatvneyyaqctpaagt ...
Aspergillus terreus                     1 mgrvsslalalllpavqaqqtlwgqcggigwtgptncvagaacstqnpyyaqclpgtat ...
Penicillium funiculosum (FJ000002)     1 mlrylsivaatailtgveaqqsvwgqcggqgwsgatscaagstcstlnpyyaqcipgtat ...
Neosartorya fischeri                   1 mkhlassialtlllpavqaqqtvwgqcggqgwsgptncvagaacstlnpyyaqcipgata ...
Emericella nidulans                    1 mhysasglalafllpaiqaqqtlygqcggsgwtgatscvagaacstlnqwyaqclpaatt ...
Talaromyces emersonii                  1 mrnllalapaallvgaaeaqqslwgqcggsswtgatscaagatcstinpyyaqcvpatat ...
Neurospora crassa                1 maakklllaaaltasalaapvledrqncgsawsqcggigwsgatccssgnscveinsyysqclpgaqv ...
Chaetomium globosum               1 maaklflaaalaatalaapvveerqncatlwgqcggngwngatccasgstctkqndwysqclpggav ...
Podospora anserina                               ttlaapvieerqncgsvwsqcggqgwtgatccasgstcvaqnqwysqclpgsqv ...
Magnaporthe grisea               1 masklflaaallqgalssplaveerqacaaqwgqcggqdytgptccqsgstcvvsnqwysqclpgssn ...
Fusarium oxysporum                 1 mayklilaafaatalaapveerqscsngvwaqcggqnwsgtpcctsgnkcvklndfysqcqpgsae ...
Gibberella zeae                  1 mtayklflaaafaatalaapveerqscsngvwsqcggqnwsgtpcctsgnkcvkvndfysqcqpgsad ...
Sclerotinia sclerotiorum               1 mglknvllaaaavaptvyaqgagysqcggqgwsgattcvsgftctytneyysqclpgsgg ...
Agaricus bisporus                     1 mfkfaallalaslvpgfvqaqspvwgqcggngwtgpttcasgstcvkqndfysqclpnnqa ...
Volvariella volvacea                  1 msrfsaltalllslpllaiaqsplygqcggngwtgpktcvsgatctvindwywqclpgngp ...
Polyporus arcularius                  1 mskfasllallaivpslayaqapvygqcggigwsgattcvsgsvctkqndyysqclpgaas ...
Acremonium cellulolyticus              1 mlrylsivaatailtgveaqqsvwgqcggqgwsgatscaagstcstlnpyyaqcipgtat ...
Lentinula edodes                      1 mkitstgllalssllpfalgqsqlygqcggwwsgattcvsgatctvvnayysqclpgsas ...


Trichoderma reesei                 431 saprfdshcalpdalqpaaqagawfqayfvqlltnanpsfl - END (471 aa)

Trichoderma koningii               431 saprfdshcalpdalqpapqagawfqayfvqlltnanpsfl - END (471 aa)
Hypocrea koningii                  430 saprfdshcalpdalqpapqagawfqayfvqlltnanpsfl - END (470 aa)
Trichoderma parceramosum           430 saprfdshcalpdalqpapqagawfqayfvqlltnanpsfl - END (470 aa)
Trichoderma viride                 431 saprfdshcalpdalqpapqagawfqayfvqlltnanpsfl - END (471 aa)
Hypocrea jecorina                  431 saprfdshcalpdalqpapqagawfqayfvqlltnanpsfl - END (471 aa)
Aspergillus clavatus               425 taarydahcgytdalkpapeagqwfqayfeqlltnanpaf  - END (464 aa)
Aspergillus fumigatus              415 tsprydahcgysdalqpapeagtwfqayfeqlltnanpsf  - END (545 aa)
Aspergillus nidulans               411 saarydahcgysdalqpapeagtwfqayfvqllqnanpsf  - END (450 aa)
Aspergillus niger                  420 satrydahcgysdalqpapeagtwfqayfvqlltnanpaf  - END (459 aa)
Aspergillus terreus                429 ssarydahcgysdalqpapeagtwfqayfeqllknanpaf  - END (468 aa)
Penicillium funiculosum            417 satrydfhcgysgalqpapeagtwfqayfvqlltnanpalv - END (457 aa)
Neosartorya fischeri               411 ssarydahcgysdalqpapeagtwfqayfeqlltnanpsf  - END (450 aa)
Emericella nidulans                416 saarydahcgysdalqpapeagtwfqayfvqllqnanpsf  - END (455 aa)
Talaromyces emersonii              420 tsprydyhcglsdalqpapeagtwfqayfeqlltnanplf  - END (459 aa)
Neurospora crassa                  445 satrydyhcglsdalkpapeagqwfqayfeqllknanpaf  - END (484 aa)
Chaetomium globosum                446 taarydhncgladalkpapeagqwfqayfeqlltnanppf  - END (485 aa)
Podospora anserina                 445 taarydhhcgfadalkpapeagqwfqayfeqlltnanppf  - END (484 aa)
Magnaporthe grisea                 447 taprfdhfcgtdygamsdapqagqwfqkyfemlltnanppl - END (487 aa)
Fusarium oxysporum                 422 saarydyhcglddalkpapeagtwfqayfeqlldnanpsfl - END (462 aa)
Gibberella zeae                    418 saarydyhcgidgavkpapeagtwfqayfeqllknanpsfl - END (458 aa)
Sclerotinia sclerotiorum           382 taarydfhcglsdalqpapeagtwfqayfaqlltnanpsf  - END (421 aa)
Agaricus bisporus                  399 ssprfdshcslsdahqpapeagtwfqayfetlvananpal  - END (438 aa)
Volvariella volvacea               403 ssprydshcglsdatpnapeagqwfqayfetlvrnasppl  - END (442 aa)
Polyporus arcularius               415 ssprfdstcslsdatqpapeagtwfqtyfetlvskanppl  - END (454 aa)
Acremonium cellulolyticus          417 satrydfhcgysdalqpapeagtwfqayfvqlltnanpalv - END (457 aa)
Lentinula edodes                   405 ssprydahcglpdatpnapeagtwfqayfetlvekanppl  - END (444 aa)
```

FIGURE 5

| Variant | Improvement factor (Bradford) | Improvement factor (ELISA) | Genotype |
|---|---|---|---|
| Wildtype | 1.00 | 1.00 | - |
| 1-A | 1.17 | 1.00 | Y53Q, S54V |
| 1-B | 1.21 | 1.10 | A65P, A66Y |
| 1-C | 1.12 | 1.12 | Y53A, S54V |
| 1-D | 1.16 | 1.27 | Q37I, N38K |
| 1-E | 1.43 | 1.24 | H438N |
| 1-F | 1.2 | 1.29 | H438S |
| 2-A | 1.56 | 1.43 | Y53Q, S54V, H438S |
| 2-B | 1.70 | 1.49 | Y53A, S54V, H438N |
| 2-C | 1.56 | 1.56 | Q37I, N38K, A65P, A66Y,H438S |
| 2-D | 1.65 | 1.87 | Q37I, N38K, Y53A, S54V, A65P, A66Y, H438S |

FIGURE 7

| | Improvement factor |
|---|---|
| Variant 1-E | 1.25 |
| Variant 2-B | 1.40 |
| Variant 2-D | 2.00 |

FIGURE 11

CBH_01_for 5`-
ATGATTGTCGGCATTCTCACCACGCTGGCTACGCTGGCCACACTCGCAGCTAGTGTG
CCTCTAGAGGAGCGGCAAGCTTGCTCAAGCGTC (SEQ ID NO.3)

CBH_02_rev 5'- TCTAGCCACATAAAAGAGGGAACCTTTGC (SEQ ID NO.4)

CBH_03_for 5'- TCCCTCTTTTATGTGGCTAGATACTCTTGACAAGACCCCTCTCATG
(SEQ ID NO.5)

CBH_04_rev 5'-
GGTCACCAGGTTGGCAAGAGAGTCAGGCTCAATAACCAGGAGGGTCCGGATATCGG
AA (SEQ ID NO.6)

CBH_05_for 5'-
CTGACTCTCTTGCCAACCTGGTGACCAACCTCGGTACTCCAAAGTGTGCCAA
(SEQ ID NO.7)

CBH_06_rev 5'- TTACAGGAACGATGGGTTTGCGTTTGTGAG (SEQ ID NO.8)

SEQUENCE LISTING

```
<160> NUMBER OF SEQ ID NOS: 8

<210> SEQ ID NO 1
<211> LENGTH: 471
<212> TYPE: PRT
<213> ORGANISM: Trichoderma reesei
```

-continued

<400> SEQUENCE: 1

```
Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415
```

-continued

```
Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470


<210> SEQ ID NO 2
<211> LENGTH: 471
<212> TYPE: PRT
<213> ORGANISM: Trichoderma reesei

<400> SEQUENCE: 2

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320
```

-continued

```
Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470


<210> SEQ ID NO 3
<211> LENGTH: 90
<212> TYPE: DNA
<213> ORGANISM: Artificial
<220> FEATURE:
<223> OTHER INFORMATION: Primer

<400> SEQUENCE: 3

atgattgtcg gcattctcac cacgctggct acgctggcca cactcgcagc tagtgtgcct     60

ctagaggagc ggcaagcttg ctcaagcgtc                                      90


<210> SEQ ID NO 4
<211> LENGTH: 29
<212> TYPE: DNA
<213> ORGANISM: Artificial
<220> FEATURE:
<223> OTHER INFORMATION: Primer

<400> SEQUENCE: 4

tctagccaca taaaagaggg aacctttgc                                       29


<210> SEQ ID NO 5
<211> LENGTH: 46
<212> TYPE: DNA
<213> ORGANISM: Artificial
<220> FEATURE:
<223> OTHER INFORMATION: Primer

<400> SEQUENCE: 5

tccctctttt atgtggctag atactcttga caagacccct ctcatg                    46


<210> SEQ ID NO 6
<211> LENGTH: 58
<212> TYPE: DNA
<213> ORGANISM: Artificial
<220> FEATURE:
<223> OTHER INFORMATION: Primer

<400> SEQUENCE: 6

ggtcaccagg ttggcaagag agtcaggctc aataaccagg agggtccgga tatcggaa       58
```

-continued

```
<210> SEQ ID NO 7
<211> LENGTH: 52
<212> TYPE: DNA
<213> ORGANISM: Artificial
<220> FEATURE:
<223> OTHER INFORMATION: Primer

<400> SEQUENCE: 7

ctgactctct tgccaacctg gtgaccaacc tcggtactcc aaagtgtgcc aa           52


<210> SEQ ID NO 8
<211> LENGTH: 30
<212> TYPE: DNA
<213> ORGANISM: Artificial
<220> FEATURE:
<223> OTHER INFORMATION: Primer

<400> SEQUENCE: 8

ttacaggaac gatgggtttg cgtttgtgag                                    30
```

POLYPEPTIDES HAVING CELLOBIOHYDROLASE II ACTIVITY

This application is a National Stage of PCT/EP2009/008792, filed. Dec. 9, 2009 which claims priority to U.S. Provisional Application No. 61/121,366, filed Dec. 10, 2008, the disclosures of which are incorporated herein by reference in their entirety.

FIELD OF THE DISCLOSURE

The technology provided herein relates to polypeptides having cellobiohydrolase II activity, nucleic acids encoding the polypeptides, vectors, host cells containing the nucleic acids and methods for producing the polypeptides. The polypeptides encompassed by this disclosure may be used in numerous applications including the use of the polypeptides for the production of biofuels and for the synthesis of platform chemicals or biopolymers from renewable sources.

BACKGROUND

Cellulose and hemicelluloses are important industrial raw materials and a source of renewable energy. They can be degraded and used by numerous microorganisms, including bacteria, yeast and fungi, that produce extracellular enzymes capable of hydrolysis of the polymeric substrates to monomeric sugars (Aro et al, J. Biol. Chem., vol. 276, no. 26, pp. 24309-24314, Jun. 29, 2001). As the limits of non-renewable resources approach, the potential of cellulose to become a major renewable energy resource is enormous (Krishna et al., Bioresource Tech. 77:193-196, 2001). The effective utilization of cellulose through biological processes is one approach to overcoming the shortage of foods, feeds, and fuels (Ohmiya et al., Biotechnol. Gen. Engineer. Rev. vol. 14, pp. 365-414, 1997).

The physical structure and morphology of native celluloses are complex and the fine details of its structure have been difficult to determine experimentally. However, the chemical composition of cellulose is simple, consisting of D-glucose residues linked by beta-1,4-glycosidic bonds to form linear polymers with chains length of over 10.000 glycosidic residues.

In order to be efficient, the digestion of cellulose requires several types of enzymes acting cooperatively. For example, cellulases are enzymes that hydrolyze cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([β]-D-glucoside glucohydrolase; EC 3.2.1.21) ("BG"). (Knowles et al., TIBTECH 5, 255-261, 1987; Schulein, Methods Enzymol., 160, 25, pp. 234-243, 1988).

Endoglucanases act mainly on the amorphous parts of the cellulose fibre, whereas cellobiohydrolases are also able to degrade crystalline cellulose (Nevalainen and Penttila, Mycota, 303-319, 1995). Thus, the presence of a cellobiohydrolase in a cellulase system is required for efficient solubilization of crystalline cellulose (Suumakki, et al. Cellulose 7:189-209, 2000). Beta-glucosidase acts to liberate D-glucose units from cellobiose, cello-oligosaccharides, and other glucosides (Freer, J. Biol. Chem. vol. 268, no. 13, pp. 9337-9342, 1993).

As mentioned above, cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeasts, such as *Saccharomyces cerevisiae*, lack the ability to hydrolyze cellulose. See, e.g., Aro eta., 2001; Biochemistry and Genetics of Cellulose Degradation, eds. Aubert, J. P. et al., Academic Press, 1988; Wood et al., Methods in Enzymology, vol. 160, no. 9, pp. 87-116, 1988, and Coughlan, et al.

Exo-cellobiohydrolase II (Cellobiohydrolase II, or CBH 2) refer to the cellobiohydrolases which degrade cellulose by hydrolyzing the cellobiose from the reducing end of the cellulose polymer chains. The cellobiohydrolase II group belongs to the same EC group, that is EC 3.2. 1.91, as the cellobiohydrolase I group, the difference being that cellobiohydrolase I degrade cellulose by hydrolyzing the cellobiose from the non-reducing end of the cellulose polymer chains.

The efficient enzymatic degradation of biomass is a key factor for the development of an improved second generation for the production of biofuels and synthesis of platform chemicals or biopolymers from renewable sources. Currently the most efficient hydrolytic systems are originating from fungi like *Trichoderma reesei*. They consist out of a mixture of enzymes (Minimal Enzyme Complex; MEC) which act complementary to depolymerize cellulose or hemicellulose to sugar monomers.

It is an object of the present invention to provide improved polypeptides having cellobiohydrolase II activity and polynucleotides encoding these polypeptides. The improved polypeptides may have improved thermostability and/or improved stability, but in particular improved specific activity.

SUMMARY OF THE DISCLOSURE

In a first aspect, embodiments of this disclosure provide polypeptides having cellobiohydrolase II activity, wherein said polypeptides comprise the amino acid sequence motif $$Q\underline{C}_1GGX_1X_2X_3X_4GX_5X_6X_7\underline{C}_2X_8X_9GX_{10}X_{11}\underline{C}_3X_{12}$$

$$X_{13}X_{14}NX_{15}X_{16}YX_{17}Q\underline{C}_4X_{18}PX_{19}X_{20}X_{21}$$

wherein $X_1$ is Q, N, A or S $X_2$ is N, G, S or D $X_{12}$ is Y, T, E, K, A or V $X_{13}$ is 5, Q, L, V, I or T $X_{20}$ is A, T, G, S or N $X_{21}$ is A, T, G, Q or S and $X_3$, $X_4$, $X_5$, $X_6$, $X_7$, $X_8$, $X_9$, $X_{10}$, $X_{11}$, $X_{13}$, $X_{14}$, $X_{15}$, $X_{16}$, $X_{17}$, $X_{18}$, $X_{19}$ are any amino acid, wherein the amino acid sequence motif comprises at least one variation in the amino acid sequence motif, and wherein the variation is selected from the group consisting of $X_1$ is I, $X_2$ is K, $X_{12}$ is A or Q, $X_{13}$ is V, $X_{20}$ is P, $X_{21}$ is Y, and wherein each of said at least one variations can be the same or different and can comprise a substitution, deletion or insertion.

In a further aspect, embodiments of this disclosure relate to polypeptides having cellobiohydrolase II activity, wherein said polypeptides comprise the amino acid sequence motif $$DGX_1X_2X_3X_4X_5X_6X_7RX_8DX_9X_{10}C$$

wherein
$X_1$ is T or V
$X_2$ is S or T
$X_3$ is D, N or V
$X_4$ is N, P, Q; S or T
$X_5$ is S or T
$X_6$ is A or S
$X_7$ is any amino acid
$X_8$ is F, Y,
$X_9$ is any amino acid
and
$X_{10}$ is S or N.

In still another aspect, embodiments of this disclosure provide polypeptides having cellobiohydrolase II activity comprising both above mentioned amino acid sequence motifs.

Further, embodiments of this disclosure relate to polypeptides having cellobiohydrolase II activity, wherein said polypeptide comprises a substitution or deletion at a position corresponding to one or more of residues Q37, N38, Y53, S54, A65, A66 and/or H438 in CBHII from *Trichoderma reesei* (SEQ ID NO: 1). In a further aspect, the disclosure encompasses polypeptides of, wherein the polypeptide comprises a substitution at a position corresponding to one or more of residues Q37I, N38K, Y53(A/Q), S54V, A65P, A66Y and/or H438(S/N) in CBHII from *Trichoderma reesei* (SEQ ID NO: 1). In one embodiment, the polypeptides comprise a substitution at a position corresponding to one or more of residues Q37I, N38K, Y53(A/Q), S54V, A65P, A66Y and/or H438(S/N) in CBHII from *Trichoderma reesei* (SEQ ID NO: 1). In a further embodiment the polypeptides consists essentially of the substitutions selected from the group consisting of:

a) Q37I, N38K,
b) Y53A, S54V
c) A65P, A66Y
d) H438S
e) H438N
f) Y53A, S54V, H438N
h) Y53Q, S54V, H438S
i) Y53Q, S54V
j) Q37I, N38K, A65P, A66Y, H438S
k) Q37I, N38K, Y53A, S54V, A65P, A66Y and H438S.

In a further aspect, the disclosure is related to polypeptides having cellobiohydrolase II activity, wherein said polypeptide having an amino acid sequence that varies from the amino acid sequence of the wild type CBHII from *Trichoderma reesei* (SEQ ID NO: 1), wherein the amino acid sequence of the polypeptide comprises at least one variation as compared with SEQ ID NO: 1, and wherein the at least one variation occurs at a position selected from the group consisting of positions 37, 38, 53, 54, 65, 66 and/or 438 of SEQ ID NO: 1, and wherein each of said at least one variations can be the same or different and can comprise a substitution, deletion or insertion. In one embodiment at least one variation comprises a variation of one, two, three, four, five, six or all seven of the positions selected from the group consisting of: Q37, N38, Y53, S54, A65, A66 and/or H438. In a further embodiment the at least one variation comprises a variation selected from the group consisting of Q37I, N38K, Y53A, S54V, A65P, A66Y and/or H438S. In another embodiment, the polypeptides consist essentially of the substitutions selected from the group consisting of:

a) Q37I, N38K,
b) Y53A, S54V
c) A65P, A66Y
d) H438S
e) H438N
f) Y53A, S54V, H438N
h) Y53Q, S54V, H438S
i) Y53Q, S54V
j) Q37I, N38K, A65P, A66Y, H438S
k) Q37I, N38K, Y53A, S54V, A65P, A66Y and H438S.

The polypeptides according to the present disclosure having at least one improved property as compared to the polypeptide of SEQ ID NO: 1, wherein the improved property is selected from the group consisting of increased specific activity; decreased sensitivity to one or more proteases; increased thermal activity; increased thermal stability, increased stability in an acidic pH, enhanced stability in a basic pH. In one embodiment, the polypeptides show an increased specific activity as compared to the polypeptide of SEQ. ID NO: 1. In a further embodiment, the improved property is an increased specific activity in avicellulose hydrolysis, wheat straw hydrolysis and/or glucan hydrolysis.

A further aspect of the disclosure relates to polypeptides having cellobiohydrolase II activity, wherein said polypeptides comprise a conserved amino acid sequence motif as part of a cellulose binding domain, wherein the amino acid sequence motif is $$Q\underline{C}_1GGX_1X_2X_3X_4GX_5X_6X_7\underline{C}_2X_8X_9GX_{10}X_{11}\underline{C}_3X_{12}$$

$$X_{13}X_{14}NX_{15}X_{16}YX_{17}Q\underline{C}_4X_{18}PX_{19}X_{20}X_{21}$$

wherein X is an amino acid and at least a deletion or substitution is in the position $X_1$, $X_2$, $X_{12}$, $X_{13}$, $X_{20}$ or $X_{21}$ compared to the corresponding isolated CBHII wild type sequences.

In another aspect the disclosure relates to polypeptides having cellobiohydrolase II activity, wherein said polypeptide comprises a conserved amino acid sequence motif as part of a cellulose binding domain, wherein the amino acid sequence motif is $$DGX_1X_2X_3X_4X_5X_6X_7RX_8DX_9X_{10}C$$

wherein $X_1$, $X_2$, $X_3$, $X_4$, Xs, $X_6$, $X_7$, $X_8$ and $X_9$ is any amino acid and $X_{10}$ is an amino acid except of H, F or T.

In other aspects, this disclosure relates to enzyme compositions comprising a polypeptide having CBHII activity and CBHII variants as described herein, wherein the enzyme composition is useful for, or used in, commercial applications. In one embodiment, the enzyme composition may be an animal feed composition. In other embodiments, the enzyme composition may be used in starch hydrolysis processes. In an advantageous embodiment, the variants and/or the enzyme composition may be used in alcohol fermentation processes. In further embodiments, an enzyme composition comprising a CBHII variant encompassed by this disclosure will include additional enzymes In still another aspect, embodiments of this disclosure provide nucleic acids encoding polypeptides having CBHII activity as disclosed herein, as well as vectors and host cells comprising such nucleic acids.

In a further aspect, embodiments of this disclosure relate to methods for producing the polypeptide having CBHII and CBHII variants in a host cell by transforming the host cell with a DNA construct, advantageously including a promoter having transcriptional activity in the host cell, cultivating the transformed host cell in a suitable culture medium to allow expression of said polypeptides and producing the polypeptides. The method may also include recovering the produced CBHII. In one embodiment, the host cell is a *Trichoderma* cell, such as *T. reesei*, a bacterial, a yeast or a plant cell. In embodiments described herein, the amino acid sequence of the CBHII variants shares a minimum percentage sequence identity to the amino acid sequence identity with SEQ ID NO: 1, e.g., at least 80%, at least 90%, and at least 95% amino acid sequence identity with SEQ ID NO: 1. In an advantageous embodiment of this disclosure, the CBHII variants shows one or all of the variations shown in FIG. 5.

BRIEF DESCRIPTION OF THE DRAWINGS

FIG. 2 shows wildtype sequence of *Trichoderma reesei* CBHII protein. The sequence contains an N-terminal signal sequence for secretion (underlined with solid line; amino acid 1-24) followed by a Fungal-type cellulose binding domain (="Small four-cysteine binding domain of fungi"; underlined with broken line; amino acid 31-62).

FIG. 3 shows the locations of one embodiment with beneficial mutations at positions Q37, N38, Y53, S54, A65, A66 and H438 of *Trichoderma reesei* CBHII (highlighted).

FIG. 4 shows the location of beneficial mutations leading to improved specific activity of CBHII on solid and soluble substrates at positions 37, 38, 53, 54, 65, 66 and 438. These positions are located in highly conserved motifs (identical amino acids within the sequences from 27 species marked grey).

FIG. 5 shows the identified mutations at positions 37, 38, 53, 54, 65, 66 and 438 of wildtype CBHII from *Trichoderma reesei*. The improvement factor of each variant's specific activity on avicellulose is shown.

FIG. 7 shows the performance of wildtype CBHII from *Trichoderma reesei*, variant 1-E, variant 2-B and variant 2-D during wheat straw hydrolysis. Equal amounts of each enzyme were tested. Compared to the wild type, variant 1-E has up to 1.25× improved specific activity, variant 2-B has up to 1.40× improved specific activity and variant 2-D has up to 2× improved specific activity.

FIG. 11 shows the cloning primer sequences (SEQ ID NO. 3 to 8)

DETAILED DESCRIPTION OF THIS DISCLOSURE

Figure 1:
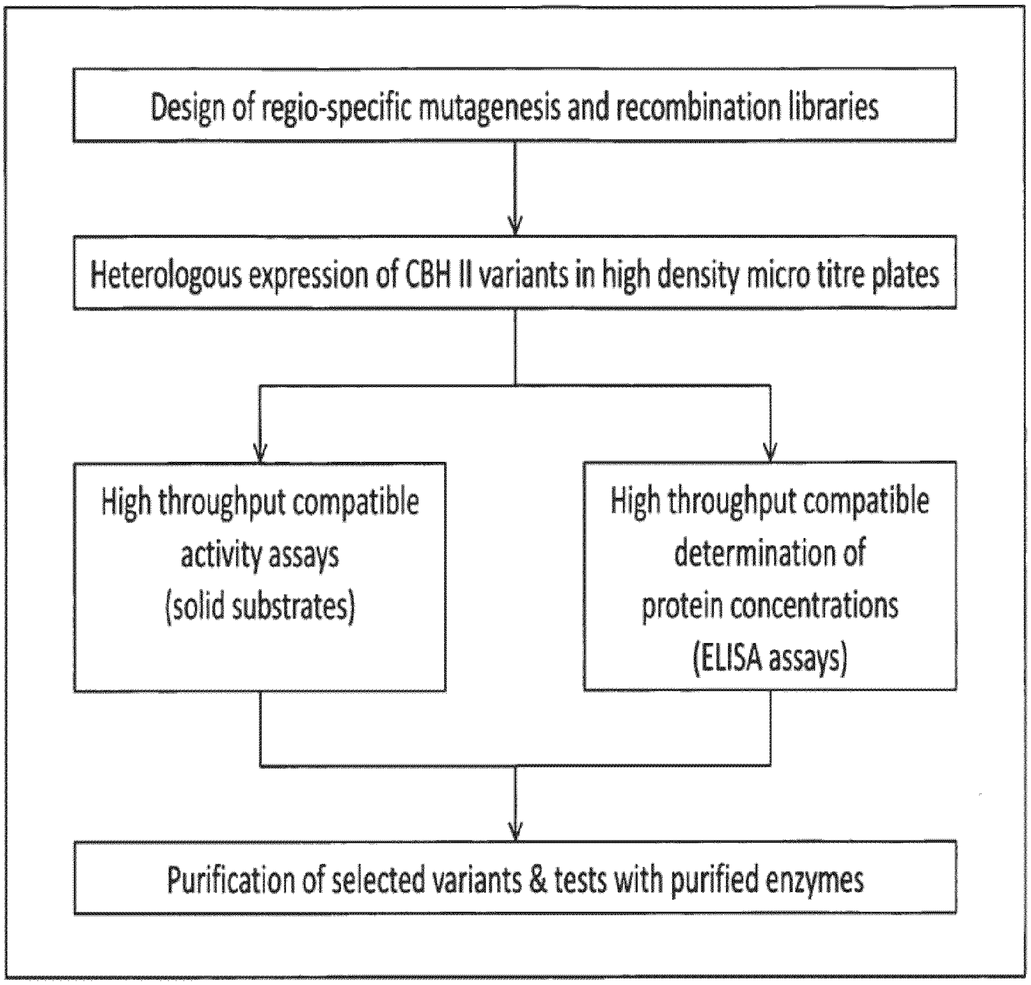
FIG. 1 shows a schematic overview of the screening strategy employed to identify CBHII variants with improved specific activity on solid substrates.

Disclosed herein are polypeptides having CBHII activity that may be used in industrial applications including the use of the variants for the production of biofuels and for the synthesis of platform chemicals or biopolymers from renewable sources. The CBHII variants have inter alia improved specific activity on solid and soluble substrates.

Amino acids are referred to herein using the name of the amino acid, the three letter abbreviation or the single letter abbreviation. The table below provides a list of the standard amino acids together with their abbreviations.

| | | |
|---|---|---|
| Alanine | A | Ala |
| Cysteine | C | Cys |
| Aspartic acid | D | Asp |
| Glutamic acid | E | Glu |
| Phenylalanine | F | Phe |
| Glycine | G | Gly |
| Histidine | H | His |
| Isoleucine | I | Ile |
| Lysine | K | Lys |
| Leucine | L | Leu |
| Methionine | M | Met |
| Asparagine | N | Asn |
| Proline | P | Pro |
| Glutamine | Q | Gln |
| Arginine | R | Arg |
| Serine | S | Ser |
| Threonine | T | Thr |
| Valine | V | Val |
| Tryptophan | W | Trp |
| Tyrosine | Y | Tyr |
| Cysteine | C | Cys |
| Aspartic acid | D | Asp |

In addition to the specific amino acid variations and nucleic acids encoding the variations, conservative amino acid substitutions of the variations are provided herein. Such substitutions are those which are conservative, for example, wherein the variant amino acid is replaced by another amino acid of the same general type. Amino acids can be classified as acidic, basic, neutral and polar, or neutral and nonpolar and/or aromatic, depending on their side chain. Preferred substitutions of a variant amino acid position include those that have one or more classifications that are the same as the variant amino acid at that position. Thus, in general, amino acids Lys, Arg, and His are basic; amino acids aspartic and glutamic are acidic; amino acids Ser, Thr, Cys, Gln, and Asn are neutral polar; amino acids Gly, Ala, Val, Ile, and Leu are nonpolar aliphatic, and amino acids Phe, Trp, and Tyr are aromatic. Gly and Ala are small amino acids and Val, Ile and Leu are alipathic amino acids.

Unless defined otherwise herein, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

DEFINITIONS

It must be noted that as used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

Although any methods and materials similar or equivalent to those described herein can be used in the practice or testing of the present disclosure, exemplary and advantageous methods and materials are now described. All publications mentioned herein are incorporated herein by reference to the extent necessary to disclose and describe the methods and/or materials connected with the disclosure for which the publications are cited.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

The term "polypeptide" as used herein refers to a compound made up of a single chain of amino acid residues linked by peptide bonds. The term "protein" as used herein may be synonymous with the term "polypeptide". In the present disclosure and claims, the conventional one-letter and three-letter codes for amino acid residues are used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

"Variant" means a protein which is derived from a precursor protein (e.g., the native protein) by addition of one or more amino acids to either or both the C- and N-terminal end, substitution of one or more amino acids at one or a number of different sites in the amino acid sequence, or deletion of one or more amino acids at either or both ends of the protein or at one or more sites in the amino acid sequence. The preparation of an enzyme variant is preferably achieved by modifying a DNA sequence which encodes for the native protein, transformation of the modified DNA sequence into a suitable host, and expression of the modified DNA sequence to form the variant enzyme. The polypeptide having CBHII activity according to the present disclosure can be a variant of a CBHII enzyme which includes peptides comprising altered amino acid sequences in comparison with a precursor enzyme amino acid sequence wherein the polypeptide and/or the variant CBHII enzyme retains the characteristic cellulolytic nature of the precursor enzyme but which may have altered properties in some specific aspect. For example, a variant CBHII enzyme may have an increased specific activity, an increased pH optimum and/or increased temperature or oxidative stability but will retain its characteristic cellulolytic activity. It is contemplated that the polypeptides and the variants according to the present disclosure may be derived from a DNA fragment encoding a cellulase variant CBHII enzyme wherein the functional activity of the expressed cellulase variant is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained. The terms variant, derivative and polypeptide having CBHII activity may be used interchangeably herein.

The term "cellobiohydrolase II activity" or "CBHII activity" is defined herein as a cellulose 1,4-beta-cellobiosidase (also referred to as Exo-glucanase, Exo-cellobiohydrolase or 1,4-beta-cellobiohydrolase) activity, as defined in the enzyme class EC 3.2. 1.91 or CAZy Family Glycoside Hydrolase Family 6, which catalyzes the hydrolysis of 1,4-beta-D-glucosidic linkages in cellulose and cellotetraose, releasing cellobiose from the reducing ends of the chains.

The term "CBHII" or "cellobiohydrolase II" refers to a protein or polypeptide which has cellobiohydrolase II activity.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "CBHII expression" refers to transcription and translation of the cbh2 gene or variants thereof, the products of which include precursor RNA, mRNA, polypeptide, post-translationally processed polypeptides, and derivatives thereof, including CBHII from related species (see FIG. 10) such as *Trichoderma koningii, Hypocrea jecorina* (also known as *Trichoderma longibrachiatum* or *Trichoderma reesei*) and *Hypocrea schweinitzii*. By way of example, assays for CBHII expression include Western blot for CBHII protein, Northern blot analysis and reverse transcriptase polymerase chain reaction (RT-PCR) assays for cbh2 mRNA, and Phosphoric Acid Swollen Cellulose and PAHBAH assays as described in the following: (a) PASC: (Karlsson, J. et al. (2001), Eur. J. Biochem, 268, 6498-6507, Wood, T. (1988) in Methods in Enzymology, Vol. 160. Biomass Part a Cellulose and Hemicellulose (Wood, W. & Kellog, S. Eds.), pp. 19-25, Academic Press, San Diego, Calif., USA) and (b) PAHBAH: (Lever, M. (1972) Analytical Biochemistry, 47, 273, Blakeney, A. B. & Mutton, L. L. (1980) Journal of Science of Food and Agriculture, 31, 889, Henry, R. J. (1984) Journal of the Institute of Brewing, 90, 37). [76] The term "alternative splicing" refers to the process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

Figure 10:
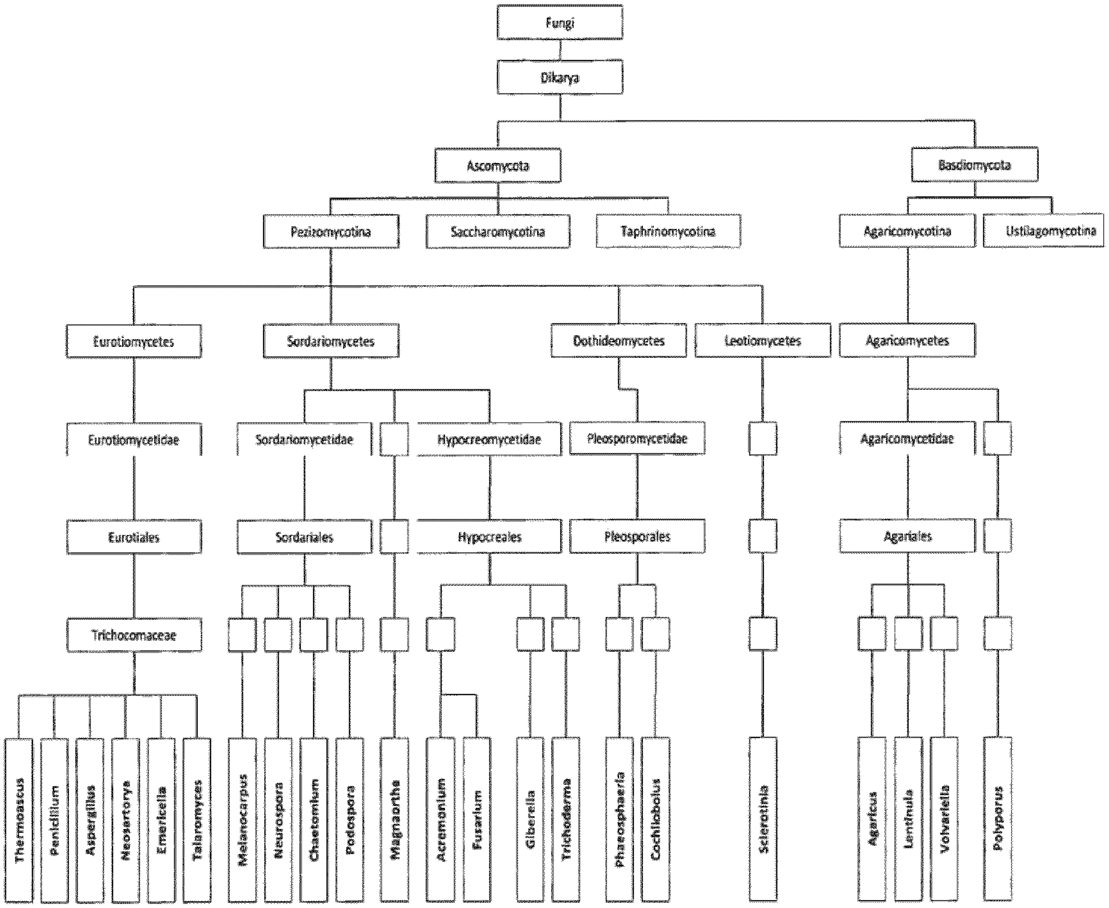
FIG. 10 shows the phylogentetic tree of the fungi according to the present disclosure.

The term "fungi" means any fungi including all filamentous fungi recognized by those of skill in the art. Examples for the fungis are shown in FIG. 10 including Ascomycota and Basidomycota, including Eurotimycetes (e.g. the general *Thermoascus, Peniclillium, Aspergillus, Neosartorya, Emericella, Talaromyces*), Sordariomycetes (e.g. *Melanocarpus, Neurospora, Chaetomium, Podospora, Magnaporthe, Acremonium, Fusarium, Giberella, Trichoderma*), Leotiomycetes (e.g. *Sclerotinia*) and Agaricomycetes (e.g. *Agaricus, Lentinula, Volvariella, Polyporus*). The sequences (FIG. 4) used for the alignment originate from *Trichoderma reesei, Trichoderma kongii, Hypocrea kongii, Trichoderma parceramosum, Trichoderma viride, Hypocrea jecorina, Aspergillus clavatus, Aspergillus fumigates, Aspergillus nidulans, Aspergillus niger, Aspergillus terreus, Penicillium funiculosum, Neosartorya fischeri, Emericella nidulans, Talaromyces emersonii, Neurospora crassa, Chaetomium globosum, Podospora anserine, Magnaporthe grisea, Fusarium oxysporum, Gibberella zeae, Sclerotinia sclerotiorum, Agaricus bisporus, Volvariella volvacea, Polyporus arcularius, Acremonium cellulolyticus, Lentinula edodes*. For example, the fungus can be selected from the group consisting of *Aspergillus, Trichoderma, Fusarium, Chrysospori[upsilon]m, Penicillium, Humicola, Neurospora*, or alternative sexual forms thereof such as *Emericella, Hypocrea*.

The term "cellooligosaccharide" refers to oligosaccharide groups containing from 2-8 glucose units and having [beta]-1,4 linkages, e.g., cellobiose.

The term "cellulase" refers to a category of enzymes capable of hydrolyzing cellulose polymers to shorter cello-oligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, plants and bacteria.

The term "cellulose binding domain" as used herein refers to portion of the amino acid sequence of a cellulase or a region of the enzyme that is involved in the cellulose binding activity of a cellulase or derivative thereof. Cellulose binding domains generally function by non-covalently binding the cellulase to cellulose, a cellulose derivative or other polysaccharide equivalent thereof. Cellulose binding domains permit or facilitate hydrolysis of cellulose fibers by the structurally distinct catalytic core region, and typically function independent of the catalytic core. Thus, a cellulose binding domain will not possess the significant hydrolytic activity attributable to a catalytic core. In other words, a cellulose binding domain is a structural element of the cellulase enzyme protein tertiary structure that is distinct from the structural element which possesses catalytic activity. Cellulose binding domain and cellulose binding module may be used interchangeably herein.

The term "variant cbh2 gene" or "variant CBHII" means, respectively, that the nucleic acid sequence of the wild type cbh2 gene from fungi including filamentous fungi has been altered by removing, adding, and/or manipulating the coding sequence or the amino acid sequence of the expressed protein has been modified.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in "Atlas of Protein Sequence and Structure", M. O. Dayhoff et., Suppl. 3:353-358, National Biomedical Research Foundation, Washington, D.C., which adapts the local homology algorithm of Smith and Waterman (1981) Advances in Appl. Math. 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information (http://www.ncbi.nlm.nih.gov/). Likewise, computer programs for determining percent homology are also readily available.

The term "property" or grammatical equivalents thereof in the context of a polypeptide, as used herein, refer to any characteristic or attribute of a polypeptide that can be selected or detected. These properties include, but are not limited to specific activity, oxidative stability, substrate specificity, catalytic activity, thermal stability, pH activity profile, and ability to be secreted.

As used herein, the term "purifying" generally refers to subjecting transgenic nucleic acid or protein containing cells to biochemical purification and/or column chromatography.

[92] As used herein, the terms "active" and "biologically active" refer to a biological activity associated with a particular protein and are used interchangeably herein. For example, the enzymatic activity associated with a protease is proteolysis and, thus, an active protease has proteolytic activity. It follows that the biological activity of a given protein refers to any biological activity typically attributed to that protein by those of skill in the art.

The term "operably linked" refers to juxtaposition wherein the elements are in an arrangement allowing them to be functionally related. For example, a promoter is operably linked to a coding sequence if it controls the transcription of the sequence.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

The term "isolated", "recovered" or "purified" refers to a material that is removed from its original environment. The term "substantially purified" means that the material has been purified to at least a substantial degree.

A "feed" and a "food," respectively, means any natural or artificial diet, meal or the like or components of such meals intended or suitable for being eaten, taken in, digested, by an animal and a human being, respectively.

A "food or feed additive" is a compound or a multi component composition intended for or suitable for being added to food or feed. It may, but is not required to, comprise one or more compounds such as vitamins, minerals or feed enhancing enzymes and suitable carriers and/or excipients, and it is usually provided in a form that is suitable for being added to animal feed.

The term "starch liquefaction" refers to a process by which starch is converted to shorter chain and less viscous dextrins.

The term "alcohol fermentations" refers to fermentative processes in which a microorganism (e.g., a yeast) converts a substrate into a metabolite which is classified as an alcohol (e.g., ethanol or butanol).

A "promoter" is a regulatory sequence that is involved in binding RNA polymerase to initiate transcription of a gene.

"Under transcriptional control" is a term well understood in the art to indicate that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

As used herein, the terms "DNA construct," "transforming DNA" and "expression vector" are used interchangeably to refer to DNA used to introduce sequences into a host cell or organism. The DNA may be generated in vitro by PCR or any other suitable technique(s) known to those in the art. The DNA construct, transforming DNA or recombinant expression cassette can be incorporated into a plasmid, chromosome, mitochondrial DNA, plastid DNA, virus, or nucleic acid fragment. Typically, the recombinant expression cassette portion of an expression vector, DNA construct or transforming DNA includes, among other sequences, a nucleic acid sequence to be transcribed and a promoter. In preferred embodiments, expression vectors have the ability to incorporate and express heterologous DNA fragments in a host cell.

As used herein, the term "vector" refers to a polynucleotide construct designed to introduce nucleic acids into one or more cell types. Vectors include cloning vectors, expression vectors, shuttle vectors, plasmids, cassettes and the like.

The term "optimal alignment" refers to the alignment giving the highest percent identity score.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein.

"Host strain" or "host cell" refers to a suitable host for an expression vector comprising DNA according to the present disclosure. Host cells for use in the present invention can be prokaryotic cells, such as *E. coli*, or eukaryotic cells such as yeast, plant, insect, amphibian, or mammalian cells. As mentioned below, host cells can be fungi including filamentous fungi.

The terms "derived from" and "obtained from" refer to not only a CBHII produced or producible by a strain of the organism in question, but also a CBHII encoded by a DNA sequence isolated from such strain and produced in a host organism containing such DNA sequence. Additionally, the terms refers to a CBHII which is encoded by a DNA sequence of synthetic and/or cDNA origin and which has the identifying characteristics of the CBHII in question. Hence, a CBHII that is "derived from" and "obtained from" another CBHII does not necessarily mean that the CBHII has been physically derived or physically obtained from the second CBHII, but rather can also mean that the CBHII in question has been prepared using knowledge or ideas derived from knowledge of the second CBHII.

Thus, to illustrate, a naturally occurring cellulase system may be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. The purified polypeptide with CBHII activity may then be added to the enzymatic solution resulting in an enriched CBH solution. It is also possible to elevate the amount of CBH produced by a microbe using molecular genetics methods to overexpress the gene encoding CBH, possibly in conjunction with deletion of one or more genes encoding other cellulases.

For example, fungal cellulases may contain more than one CBH component. The different components generally have different isoelectric points which allow for their separation via ion exchange chromatography and the like. Either a single CBH component or a combination of CBH components may be employed in an enzymatic solution.

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present disclosure, the fungal parent cell may be a cell of a species of, but not limited to Ascomycota and Basidomycota, including Eurotimycetes (e.g. the genera *Peniclillium, Aspergillus, Neosartorya, Emericella, Talaromyces*), Sordariomycetes (e.g. the general *Thermoascus, Peniclillium, Aspergillus, Neosartorya, Emericella, Talaromyces*), Sordariomycetes (e.g. *Melanocarpus, Neurospora, Chaetomium, Podospora, Magnaporthe, Acremonium, Fusarium, Giberella, Trichoderma*), Leotiomycetes (e.g. *Sclerotinia*) and Agaricomycetes (e.g. *Agaricus, Lentinula, Volvariella, Polyporus*). Examples for the fungi (shown in FIG. 4) are *Trichoderma reesei, Trichoderma kongii, Hypocrea kongii, Trichoderma parceramosum, Trichoderma viride, Hypocrea jecorina, Aspergillus clavatus, Aspergillus fumigates, Aspergillus nidulans, Aspergillus niger, Aspergillus terreus, Penicillium funiculosum, Neosartorya fischeri, Emericella nidulans, Talaromyces emersonii, Neurospora crassa, Chaetomium globosum, Podospora anserine, Magnaporthe grisea, Fusarium oxysporum, Gibberella zeae, Sclerotinia sclerotiorum, Agaricus bisporus, Volvariella volvacea, Polyporus arcularius, Acremonium cellulolyticus, Lentinula edodes*. For example, the fungus can be selected from the group consisting of *Aspergillus, Trichoderma, Fusarium, Chrysospori[upsilon]m, Penicillium, Humicola, Neurospora*, or alternative sexual forms thereof such as *Emericella, Hypocrea*. As used herein, the term "*Trichoderma*" or "*Trichoderma* sp." refers to any fungal strains which have previously been classified as *Trichoderma* or are currently classified as *Trichoderma.*

In one preferred embodiment, the filamentous fungal parent cell is a *Trichoderma reesei* cell.

Cellulases are known in the art as enzymes that hydrolyze cellulose (beta-1,4-glucan or beta D-glucosidic linkages) resulting in the formation of glucose, cellobiose, cellooligosaccharides, and the like. As set forth above, cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG"). (Knowles, et al., TIBTECH 5, 255-261, 1987; Schulein, 1988).

Certain fungi produce complete cellulase systems which include exo-cellobiohydrolases or CBH-type cellulases, endoglucanases or EG-type cellulases and beta-glucosidases or BG-type cellulases (Schulein, 1988). However, sometimes these systems lack CBH-type cellulases and bacterial cellulases also typically include little or no CBH-type cellulases. In addition, it has been shown that the EG components and CBH components synergistically interact to more efficiently degrade cellulose. See, e.g., Wood, 1985. The different components, i.e., the various endoglucanases and exocellobiohydrolases in a multi-component or complete cellulase system, generally have different properties, such as isoelectric point, molecular weight, and degree of glycosylation, substrate specificity and enzymatic action patterns.

It is believed that endoglucanase-type cellulases hydrolyze internal beta-1,4-glucosidic bonds in regions of low crystallinity of the cellulose and exo-cellobiohydrolase-type cellulases hydrolyze cellobiose from the reducing or non-reducing end of cellulose. It follows that the action of endoglucanase components can greatly facilitate the action of exocellobiohydrolases by creating new chain ends which are recognized by exo-cellobiohydrolase components. Further, beta-glucosidase-type cellulases have been shown to catalyze the hydrolysis of alkyl and/or aryl [beta]-D-glucosides such as methyl [beta]-D-glucoside and p-nitrophenyl glucoside as well as glycosides containing only carbohydrate residues, such as cellobiose. This yields glucose as the sole product for the microorganism and reduces or eliminates cellobiose which inhibits cellobiohydrolases and endoglucanases.

Cellulases also find a number of uses in detergent compositions including to enhance the production of biofuels and for the synthesis of platform chemicals or biopolymers from renewable sources cleaning ability and as a softening agent and to improve the feel of cotton fabrics (Hemmpel, ITB Dyeing/Printing/Finishing 3:5-14, 1991; Tyndali, Textile Chemist and Colorist 24:23-26, 1992; Kumar et al., Textile Chemist and Colorist, 29:37-42, 1997).

Cellulases have been shown to be useful in degradation of cellulase biomass to ethanol (wherein the cellulase degrades cellulose to glucose and yeast or other microbes further ferment the glucose into ethanol), in the treatment of mechanical pulp (Pere et al., In Proc. Tappi Pulping Conf., Nashville, Tenn., 27-31, pp. 693-696, 1996) and for use as a feed additive (WO 91/04673).

Most CBHs and EGs have a multidomain structure consisting of a core domain separated from a cellulose binding domain (CBD) by a linker peptide (Suurnakki et al., 2000). The core domain contains the active site whereas the CBD interacts with cellulose by binding the enzyme to it (van Tilbeurgh et al., .FEBS Lett. 204:223-227, 1986; Tomme et al., Eur. J. Biochem. 170:575-581, 1988). The CBDs are particularly important in the hydrolysis of crystalline cellulose. It has been shown that the ability of cellobiohydrolases to degrade crystalline cellulose clearly decreases when the CBD is absent (Under and Teeri, J. Biotechnol. 57:15-28, 1997).

In one embodiment this disclosure provides for the expression of genes encoding for a polypeptide having CBHII activity and CBHII variants under control of a promoter functional in a filamentous fungus. Therefore, this invention relies on routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Ausubel et al., eds., Current Protocols in Molecular Biology (1994)).

Any method known in the art that can introduce mutations is contemplated by the present invention.

The present disclosure relates to the expression, purification and/or isolation and use of polypeptides having CBHII activity and variant CBHII. These enzymes are preferably prepared by recombinant methods utilizing the cbh2 gene from *T. reseei.*

The fermentation broth may be used with or without purification.

After the isolation and cloning of the cbh2 gene from *T. reseei*, other methods known in the art, such as site directed mutagenesis, are used to make the substitutions, additions or deletions that correspond to substituted amino acids in the expressed polypeptides and CBHII variant. Again, site directed mutagenesis and other methods of incorporating amino acid changes in expressed proteins at the DNA level can be found in Sambrook, et al. and Ausubel, et al.

DNA encoding an amino acid sequence variant of the *T. reseei* CBHII is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the *T. reseei* CBHII.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide, i.e., *T. reseei* CBHII. See Higuchi, in PCR Protocols, pp. 177-183 (Academic Press, 1990); and Vallette et al., Nuc. Acids Res. 17:723-733 (1989). See, also, for example Cadwell et al., PCR Methods and Applications, Vol 2, 28-33 (1992). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a variant CBH 2 can be determined, and a nucleic acid sequence encoding such amino acid sequence variant can be generated synthetically.

The polypeptides having CBHII activity so prepared may be subjected to further modifications, oftentimes depending on the intended use of the cellulase. Such modifications may involve further alteration of the amino acid sequence, fusion to heterologous polypeptide(s) and/or covalent modifications.

According to the present disclosure, domains are identified where beneficial mutations leading to increased specific activity of proteins with CBHII activity on solid and soluble substrates. Regarding to the CBHII wildtype protein of *Trichoderma reesei* (SEQ. NO. 1) the beneficial mutations can be located at seven positions (Q37, N38, Y53, S54, A65, A66 and H438) of CBHII.

Mutations are located in the Cellulose Binding Domain (CBD) or its close proximity. The CBD domain contains highly conserved motifs, e.g. four cysteine residues, and is widely spread among fungi. This kind of CBD is also named as "small four-cysteine binding domains of fungi". The characteristic cysteins and the spacing between them is highly conserved (see FIG. 4). The motif consists out of Q $C_1GGX_1X_2X_3X_4GX_5X_6X_7C_2X_8X_9GX_{10}X_{11}C_3X_{12}X_{13}X_{14}NX_{15}X_{16}YX_{17}QC_4X_{18}PX_{19}X_{20}X_{21}$, wherein X is an amino acid.

The beneficial positions can be clearly located with respect to the four cysteins ($C_1$, $C_2$, $C_3$, $C_4$; underlined) and other highly conserved residues of the motif. This allows their unambiguous localization in CBDs of other fungi (see FIG. 4). In one embodiment, the first two residues (Q37 and N38 of CBHII of *Trichoderma reesei*) are following C-terminally ($X_1$ and $X_2$) of the sub-motif $QC_1GGX_1X_2$. The second pair of beneficial positions (Y53 and S54 of CBHII of *Trichoderma reesei*) can be located at positions $X_{12}$ and $X_{13}$ of the sub-motif $C_3X_{12}X_{13}X_{14}N$. The third pair of beneficial positions can be located at positions $X_{20}$ and $X_{21}$ of the sub-motif $QC_4X_{18}PX_{19}X_{20}X_{21}$.

In one embodiment a beneficial position can be located at $X_3$ of the conserved motif $RX_1DX_2X_3C$. In a further embodiment the mutation is located at position H438 of CBHII of *Trichoderma reesei*. Again it is possible to unambiguously localize this position and the motif in related sequences because of its conserved arginine, aspartate and cysteine residues.

In another embodiment a beneficial position can be located at $X_{10}$ of the conserved motif $DGX_1X_2X_3X_4X_5X_6X_7RX_8DX_9X_{10}C$, wherein $X_1$, $X_2$, $X_3$, $X_4$, $X_5$, $X_6$, $X_7$, $X_8$ and $X_9$ is any amino acid and $X_{10}$ is an amino acid except of H, F or T. In one embodiment $X_{10}$ is S or N.

The CBHII wildtype protein of *Trichoderma reesei* contains an N-terminal signal sequence for secretion (amino acids 1-24; underlined with solid line) followed by a fungal-type cellulose binding domain (CBD; amino acids 31-62; see FIG. 2). The CBD domain contains highly conserved motifs, e.g. four cysteine residues, and is widely spread among fungi. This kind of CBD is also named as "small four-cysteine binding domains of fungi".

In one embodiment of the present disclosure seven positions are identified where mutations increased the specific activity of the wild type CBHII protein of *Trichoderma reesei* on solid and soluble substrates (highlighted positions in FIG. 3). These positions included six positions which are located in or in very close proximity to the CBD (positions Q37, N38, Y53, S54, A65 and A66). One identified position (H438) was located in the C-terminal part of the protein. It is also located in a highly conserved motif of the protein.

In another embodiment seven positions are identified where mutations increased the specific activity of the CBHII protein on solid and soluble substrates (highlighted positions in FIG. 3). The beneficial mutations at positions Q37, N38, Y53, S54, A65, A66 and H438 (bold letters in FIG. 4) are located in highly conserved motifs (identical amino acids within the sequences from species marked grey in FIG. 4). These motifs are present in numerous proteins from Ascomycota and Basidomycota, including Eurotimycetes (e.g. the general *Thermoascus, Peniclillium, Aspergillus, Neosartorya, Emericella, Talaromyces*), Sordariomycetes (e.g. *Melanocarpus, Neurospora, Chaetomium, Podospora, Magnaporthe, Acremonium, Fusarium, Giberella, Trichoderma*), Leotiomycetes (e.g. *Sclerotinia*) and Agaricomycetes (e.g. *Agaricus, Lentinula, Volvariella, Polyporus*). The 27 sequences used for the alignment originate from *Trichoderma reesei, Trichoderma kongii, Hypocrea kongii, Trichoderma parceramosum, Trichoderma viride, Hypocrea jecorina, Aspergillus clavatus, Aspergillus fumigates, Aspergillus nidulans, Aspergillus niger, Aspergillus terreus, Penicillium funiculosum, Neosartorya fischeri, Emericella nidulans,*

*Talaromyces emersonii, Neurospora crassa, Chaetomium globosum, Podospora anserine, Magnaporthe grisea, Fusarium oxysporum, Gibberella zeae, Sclerotinia sclerotiorum, Agaricus bisporus, Volvariella volvacea, Polyporus arcularius, Acremonium cellulolyticus, Lentinula edodes.*

In one embodiment seven positions are identified where mutations increased the specific activity of the CBHII protein on solid and soluble substrates (highlighted positions in FIG. 3). These positions included six positions which are located in or in very close proximity to the CBD (positions Q37, N38, Y53, S54, A65 and A66). One identified position (H438) was located in the C-terminal part of the protein. It is also located in a highly conserved motif of the protein. Beneficial mutations included Q37I, N38K, Y53A, Y53Q, S54V, A65P, A66Y, H438S and H438N. The improvement factors generated from either protein concentration measurement via Bradford or ELISA were very similar and showed a good correlation. In FIG. 5 examples for improved variants are shown having one to seven mutations (e.g. variant 1-E and variant 2-D).

The polypeptides having CBHII activity and the CBHII variants of this disclosure can have amino acid sequences that are derived from the amino acid sequence of a precursor CBHII. The amino acid sequence of the polypeptides having CBHII activity and the CBHII variants differs from the precursor CBHII amino acid sequence by the substitution, deletion or insertion of one or more amino acids of the precursor amino acid sequence. In a preferred embodiment, the precursor CBHII is *Hypocrea jecorina* preferably *Trichoderma reseei*. The mature amino acid sequence of *Trichoderma reseei* CBHII is shown in FIG. 1. Thus, this disclosure is directed to polypeptides having CBHII activity and CBHII variants which contain amino acid residues at positions which are equivalent to the particular identified residue in *T. reseei* and/or other fungi shown in FIG. 4. A residue (amino acid) of an CBHII homolog is equivalent to a residue of *T. reseei* CBHII if it is either homologous (i.e., corresponding in position in either primary or tertiary structure) or is functionally analogous to a specific residue or portion of that residue in *T. reseei* CBHII (i.e., having the same or similar functional capacity to combine, react, or interact chemically or structurally). As used herein, numbering is intended to correspond to that of the mature CBHII amino acid sequence as illustrated in FIG. 1.

The amino acid position number (e.g., +51) refers to the number assigned to the mature *T. reseei* CBHII sequence presented in FIG. 2.

Alignment of amino acid sequences to determine homology is preferably determined by using a "sequence comparison algorithm." Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. ScL USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection, Visual inspection may utilize graphics packages such as, for example, MOE by Chemical Computing Group, Montreal Canada.

An example of an algorithm that is suitable for determining sequence similarity is the BLAST algorithm, which is described in Altschul, et al, J. MoI. Biol. 215:403-410 (1990). Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence that either match or satisfy some positive-valued threshold score T when aligned with a word of the same length in a database sequence. These initial neighborhood word, hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. ScL USA 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, Proc. Natl. Acad. ScL USA 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

For purposes of the present invention, the degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polynucleotide sequence comparison: GAP creation penalty of 5.0 and GAP extension penalty of 0.3.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al, 1997.)

The methods of the disclosure rely on the use cells to express polypeptides having CBHII activity and variant CBHII, with no particular method of CBHII expression required. The CBHII is preferably secreted from the cells.

The disclosure provides host cells which have been transduced, transformed or transfected with an expression vector comprising a variant CBH-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transformed with an expression vector having a promoter or biologically active promoter fragment or one or more (e.g., a series) of enhancers which functions in the host cell line, operably linked to a DNA segment encoding CBHII, such that CBHII is expressed in the cell line.

Natural or synthetic polynucleotide fragments encoding CBHII ("CBHII-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of CBHII. Any vector may be used as long as it is replicable and viable in the cells into which it is introduced. Large numbers of suitable vectors and promoters are known to those of skill in the art, and are commercially available. Cloning and expression vectors are also described in Sambrook [theta]tal., 1989, Ausubel F M et al., 1989, and Strathern et al., The Molecular Biology of the Yeast *Saccharomyces,* 1981, each of which is expressly incorporated by reference herein. Appropriate expression vectors for fungi are described in van den Hondel, C. A. M. J. J. et al. (1991) In: Bennett, J. W. and Lasure, L L (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Recombinant filamentous fungi comprising the coding sequence for variant CBHII may be produced by introducing a heterologous nucleic acid construct comprising the variant CBHII coding sequence into the cells of a selected strain of the filamentous fungi.

Once the desired form of a variant cbh2 nucleic acid sequence is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected variant cbh2 coding sequence may be inserted into a suitable vector according to well-known recombinant techniques and used to transform filamentous fungi capable of CBHII expression. Due to the inherent degeneracy of the genetic code, other nucleic acid sequences which encode substantially the same or a functionally equivalent amino acid sequence may be used to clone and express variant CBHII. Therefore it is appreciated that such substitutions in the coding region fall within the sequence variants covered by the present invention. Any and all of these sequence variants can be utilized in the same way as described herein for a parent CBH2-encoding nucleic acid sequence.

The present disclosure also includes recombinant nucleic acid constructs comprising one or more of the polynucleotides having CBHII activity and variant CBHII-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for variant cbh2: (i) in isolation; (ii) in combination with additional coding sequences; such as fusion protein or signal peptide coding sequences, where the cbh2 coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the cbh2 coding sequence is a heterologous gene.

In one aspect of the present invention, a heterologous nucleic acid construct is employed to transfer a variant CBH2-encoding nucleic acid sequence into a cell in vitro, with established filamentous fungal and yeast lines preferred. For long-term, production of variant CBHII, stable expression is preferred. It follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al.

The present invention also contemplates the use of yeast as a host cell for CBHII production. Several other genes encoding hydrolytic enzymes have been expressed in various strains of the yeast *S. cerevisiae*. These include sequences encoding for two endoglucanases (Penttila et al., Yeast vol. 3, pp 175-185, 1987), two cellobiohydrolases (Penttila et al., Gene, 63: 103-112, 1988) and one beta-glucosidase from *Trichoderma reesei* (Cummings and Fowler, Curr. Genet. 29:227-233, 1996), a xylanase from *Aureobasidlium pullulans* (Li and Ljungdahl, Appl. Environ. Microbiol. 62, no. 1, pp. 209-213, 1996), an alpha-amylase from wheat (Rothstein et al., Gene 55:353-356, 1987), etc. In addition, a cellulase gene cassette encoding the *Butyrivibrio fibrisolvens* endo-[beta]-1,4-glucanase (END1), *Phanerochaete chrysosporium* cellobiohydrolase (CBH1), the *Ruminococcus flavefaciens* cellodextrinase (CEL1) and the *Endomyces fibrilizer* cellobiase (BgH) was successfully expressed in a laboratory strain of *S. cerevisiae* (Van Rensburg et al., Yeast, vol. 14, pp. 67-76, 1998).

In general, a polypeptide having CBHII activity and variant CBHII protein produced in cell culture is secreted into the medium and may be purified or isolated, e.g., by removing unwanted components from the cell culture medium. However, in some cases, a variant CBHII protein may be produced in a cellular form necessitating recovery from a cell lysate. In such cases the variant CBHII protein is purified from the cells in which it was produced using techniques routinely employed by those of skill in the art. Examples include, but are not limited to, affinity chromatography (Tilbeurgh et al., FEBS Lett. 16:215, 1984), ion-exchange chromatographic methods (Goyal et al., Bioresource Technol. 36:37-50, 1991; Fliess et al., Eur. J. Appl. Microbiol. Biotechnol. 17:314-318, 1983; Bhikhabhai et al., J. Appl. Biochem. 6:336-345, 1984; Ellouz et al., J. Chromatography 396:307-317, 1987), including ion-exchange using materials with high resolution power (Medve et al., J. Chromatography A 808:153-165, 1998), hydrophobic interaction chromatography (Tomaz and Queiroz, J. Chromatography A 865:123-128, 1999), and two-phase partitioning (Brumbauer, et al., Bioseparation 7:287-295, 1999).

Once expression of a given variant CBHII protein is achieved, the CBHII protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, Methods in Enzymology, vol. 182, no. 57, pp. 779, 1990; Scopes, Methods Enzymol. 90: 479-91, 1982. The purification step(s) selected will depend, e.g., on the nature of the production process used and the particular protein produced. IX. Utility of cbh2 and CBHII it can be appreciated that the variant cbh nucleic acids, the variant CBHII protein and compositions comprising variant CBHII protein activity find utility in a wide variety applications, some of which are described below.

Since the rate of hydrolysis of cellulosic products may be increased by using a transformant having at least one additional copy of the cbh gene inserted into the genome, products that contain cellulose or heteroglycans can be degraded at a faster rate and to a greater extent. Products made from cellulose such as paper, cotton, cellulosic diapers and the like can be degraded more efficiently in a landfill. Thus, the fermentation product obtainable from the transformants or the transformants alone may be used in compositions to help degrade by liquefaction a variety of cellulose products.

Separate saccharification and fermentation is a process whereby cellulose present in biomass, e.g., wheatstraw, corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another approach, the variant CBH type cellulase of the invention finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

A large variety of feedstocks may be used with the inventive variant CBH and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

A cellulase composition containing an enhanced amount of cellobiohydrolase finds utility in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Ethanol can be produced via saccharification and fermentation processes from cellulosic biomass such as trees, herbaceous plants, municipal solid waste and agricultural and forestry residues. However, the ratio of individual cellulase enzymes within a naturally occurring cellulase mixture produced by a microbe may not be the most efficient for rapid conversion of cellulose in biomass to glucose. It is known that endoglucanases act to, produce new cellulose chain ends which themselves are substrates for the action of cellobiohydrolases and thereby improve the efficiency of hydrolysis of the entire cellulase system. Therefore, the use of increased or optimized cellobiohydrolase activity may greatly enhance the production of ethanol.

Thus, the inventive cellobiohydrolase finds use in the hydrolysis of cellulose to its sugar components. In one embodiment, a variant cellobiohydrolase is added to the biomass prior to the addition of a fermentative organism. In a second embodiment, a variant cellobiohydrolase is added to the biomass at the same time as a fermentative organism. Optionally, there may be other cellulase components present in either embodiment.

In another embodiment the cellulosic feedstock may be pretreated. Pretreatment may be by elevated temperature and the addition of either of dilute acid, concentrated acid or dilute alkali solution. The pretreatment solution is added for a time sufficient to at least partially hydrolyze the hemicellulos components and then neutralized. Extraction of lignin with processes employing organic solvents may be an alternative pretreatment prior to enzymatic treatment of the celluloses and hemicelluloses.

The major product of CBHII action on cellulose is cellobiose which is available for conversion to glucose by BG activity (for instance in a fungal cellulase product). Either by the pretreatment of the cellulosic biomass or by the enzymatic action on the biomass, other sugars, in addition to glucose and cellobiose, can be made available from the biomass. The hemi-cellulose content of the biomass can be converted (by hemi-cellulases) to sugars such as xylose, galactose, mannose and arabinose. Thus, in a biomass conversion process, enzymatic saccharification can produce sugars that are made available for biological or chemical conversions to other intermediates or end-products. Therefore, the sugars generated from biomass find use in a variety of processes in addition to the generation of ethanol. Examples of such conversions are fermentation of glucose to ethanol (as reviewed by M. E. Himmel et al. pp 2-45, in "Fuels and Chemicals from Biomass", ACS Symposium Series 666, ed B. C. Saha and J. Woodward, 1997) and other biological conversions of glucose to 2,5-diketo-D-gluconate (U.S. Pat. No. 6,599,722), lactic acid (R. Datta and S-P. Tsai pp 224-236, ibid), succinate (R. R. Gokarn, M. A. Eiteman and J. Sridhar pp 237-263, ibid), 1,3-propanediol (A-P. Zheng, H. Biebl and W-D. Deckwer pp 264-279, ibid), 2,3-butanediol (C S. Gong, N. Cao and G T. Tsao pp 280-293, ibid), and the chemical and biological conversions of xylose to xylitol (B. C. Saha and R. J. Bothast pp 307-319, ibid). See also, for example, WO 98/21339.

The detergent compositions of this invention may employ besides the cellulase composition (irrespective of the cellobiohydrolase content, i.e., cellobiohydrolase-free, substantially cellobiohydrolase-free, or cellobiohydrolase enhanced), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. The cellulase composition as described above can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent.

In addition the variant CBH2 nucleic acid sequence finds utility in the identification and characterization of related nucleic acid sequences. A number of techniques useful for determining (predicting or confirming) the function of related genes or gene products include, but are not limited to, (A) DNA/RNA analysis, such as (1) overexpression, ectopic expression, and expression in other species; (2) gene knockout (reverse genetics, targeted knock-out, viral induced gene silencing (VIGS, see Baulcombe, 100 Years of Virology, Calisher and Horzinek eds., Springer-Verlag, New York, N.Y. 15:189-201, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

All patents, patent applications, articles and publications mentioned herein, are hereby expressly incorporated herein by reference.

The polypeptides according to the present disclosure can be variants of wild type CBHII and can be used for the breakdown of biomass and the enzymatic hydrolysis of cellulose and hemicellulose polymers which leads to sugar monomers which can be used to produce biofuels, platform chemicals, biopolymers and other chemicals.

These chemicals comprise C6-based chemicals (e.g. glucose, fructose, galactose, mannose, mannitol, sorbitol, glucaric acid), C5-based chemicals (e.g. xylose, arabinose, xylitol, glutamic acid, levulinic acid, itaconic acid), C4-based chemicals (e.g. butane, butanol, succinic acid, aspartic acid, hydroxybutyrolactone, malic acid, fumaric acid, erythritol), C3-based chemicals (e.g. propane, propanol, 1,3-propanediol, 3-hydroxypropionic acid, glycerol, lactic acid, pyruvic acid), C2-based chemicals (e.g. ethane, ethanol, acetic acid) or C1-based chemicals (e.g. methane, methanol, formic acid).

The sugar monomers which are produced during the enzymatic hydrolysis may be used directly, in fermentations or in chemical reactions.

The sugar monomers and the products of a fermentation or chemical reaction which utilizes the sugar monomers may be used as platform chemicals, as building blocks for bio-polymers, in the chemical industry, as feed additives, as food additives, for biofuels and/or for biogas.

The sugar monomers can be used to produce solid, liquid or gaseous products.

Surprisingly, it was found that a critical factor to improve the optimization of key enzymes from the MEC is to improve its overall performance. This procedure consists out of two phases: During the first phase the most limiting enzyme activities are identified and during a second step they are optimized.

According to the present disclosure, surprisingly it was found that with the analysis of MEC mixtures from *Trichoderma reesei* the cellobiohydrolase II (CBHII) activity is limiting during hydrolysis of solid biomasses.

According to the present disclosure, one approach to optimize MEC's was the increase of expression and secretion of key enzymes. Due to limiting secretion capabilities this approach is limited. Current production strains, which are already optimized for secretion of high amounts of MEC enzymes, are still not good enough for economically viable MEC production.

Surprisingly it was found, that the polypeptides having CBHII activity according to the present disclosure show for example a highly improved specific activity of CBHII on solid and soluble substrates. For example, the improved specify can be at least as twice compared to wildtype CBHII from *Trichoderma reesei* at least in the hydrolysis of wheat straw and/or avicelluloses.

One advantage is that providing the polypeptides having CBHII activity according to the present disclosure allows straightforward improvement of MECs without improving the overall expression and secretion capability of the production strains.

In one embodiment, the polypeptides having CBHII activity according to the present disclosure comprise one or more variations (including substitutions, insertions and deletions) from the amino acid sequence of wild type CBHII from *Trichoderma reesei* (SEQ ID NO: 1).

In order to identify variants with improved specific activity on solid substrates regio-specific libraries of CBHII were designed, cloned and heterologously expressed in yeast (FIG. 1). Screening for variants having improved specific activity of CBHII involved the screening of these libraries in high density micro titre plates.

High throughput activity assays with solid substrates and high throughput protein determinations via ELISA were performed in parallel. To assure predictive screens it was essential to have avicellulose or wheat straw included from the very first beginning. It was also very important to quantify the protein concentrations in parallel to the activity assays to prevent selection of expression variants.

Variants showing improvements were purified and re-evaluated in benchtop tests. This thorough analysis assured that only beneficial mutations were used for the next round of Directed Evolution.

In one embodiment the CBHII wildtype protein of *Trichoderma reesei* was used (FIG. 2) which contains an N-terminal signal sequence for secretion (amino acids 1-24; underlined with solid line) followed by a fungal-type cellulose binding domain (CBD; amino acids 31-62; underlined with broken line). The CBD domain contains highly conserved motifs, e.g. four cysteine residues, and is widely spread among fungi. This kind of CBD is also named as "small four-cysteine binding domains of fungi". DIREVO's protein engineering strategy involved a set of regio-specific libraries targeting this region and in its proximity. Other pre-selected regions were evaluated by region-specific libraries as well.

In one embodiment, during the Protein engineering of CBHII wildtype protein of *Trichoderma reesei* sets of regio-specific libraries were screened and variants having improved specific activity on solid (and soluble) substrates were identified. In one embodiment, all identified beneficial mutations are located at seven positions (Q37, N38, Y53, S54, A65, A66 and H438) of CBHII of *Trichoderma reesei*.

In one embodiment of the present disclosure six of seven mutations are located in the Cellulose Binding Domain (CBD) or its close proximity. The CBD domain contains highly conserved motifs, e.g. four cysteine residues, and is widely spread among fungi. This kind of CBD is also named as "small four-cysteine binding domains of fungi". The characteristic cysteins and the spacing between them is highly conserved (see FIG. 4). The motif consists out of Q $C_1GGX_1X_2X_3X_4GX_5X_6X_7C_2X_8X_9GX_{10}X_{11}C_3X_{12}X_{13}X_{14}NX_{15}X_{16}YX_{17}QC_4X_{18}PX_{19}X_{20}X_{21}$, wherein X stands for an amino acid.

In one embodiment seven positions are mutations which increase the specific activity of the CBHII protein on solid and soluble substrates (highlighted positions in FIG. 3). The beneficial mutations at positions Q37, N38, Y53, S54, A65, A66 and H438 (marked red in FIG. 4) are located in highly conserved motifs (identical amino acids within the sequences from 27 species marked yellow in FIG. 4). These motifs are present in numerous proteins from Ascomycota and Basidomycota, including Eurotimycetes (e.g. the general *Thermoascus, Peniclillium, Aspergillus, Neosartorya, Emericella, Talaromyces*), Sordariomycetes (e.g. *Melanocarpus, Neurospora, Chaetomium, Podospora, Magnaporthe, Acremonium, Fusarium, Giberella, Trichoderma*), Leotiomycetes (e.g. *Sclerotinia*) and Agaricomycetes (e.g. *Agaricus, Lentinula, Volvariella, Polyporus*). The sequences used for the alignment originate from *Trichoderma reesei, Trichoderma kongii, Hypocrea kongii, Trichoderma parceramosum, Trichoderma viride, Hypocrea jecorina, Aspergillus clavatus, Aspergillus fumigates, Aspergillus nidulans, Aspergillus niger, Aspergillus terreus, Penicillium funiculosum, Neosartorya fischeri, Emericella nidulans, Talaromyces emersonii, Neurospora crassa, Chaetomium globosum, Podospora anserine, Magnaporthe grisea, Fusarium oxysporum, Gibberella zeae, Sclerotinia sclerotiorum, Agaricus bisporus, Volvariella volvacea, Polyporus arcularius, Acremonium cellulolyticus, Lentinula edodes.*

In one embodiment seven mutations increased the specific activity of the CBHII protein on solid and soluble substrates (highlighted positions in FIG. 3). These positions included six positions which are located in or in very close proximity to the CBD (positions Q37, N38, Y53, S54, A65 and A66). One identified position (H438) was located in the C-terminal part of the protein. It is also located in a highly conserved motif of the protein. Beneficial mutations included Q37I, N38K, Y53A, Y53Q, S54V, A65P, A66Y, H438S and H438N. The improvement factors generated from either protein concentration measurement via Bradford or ELISA were very similar and showed a good correlation. They are shown for improved variants having between one (e.g. variant 1-E) and seven (e.g. variant 2-D) mutations.

In some embodiments, a polypeptide according to this disclosure will have altered properties. Advantageously, a polypeptide according to embodiments of this disclosure will have improved properties as compared to the wild type CBHII of SEQ. ID NO: 1.

In some embodiments of this disclosure, the host strain is genetically engineered to express heterologous CBHII or variants having CBHII activity according to this disclosure.

Host cells useful for the production of a CBHII encompassed by this disclosure include bacterial cells, fungal cells and plant cells. Host cells include both the cells and progeny of the cells and protoplasts created from the cells which may be used to produce a variant CBHII according to this disclosure.

Useful vectors including DNA constructs comprising a polynucleotide encoding a polypeptide having CBHII activity of this disclosure and transformation methods of host cells are well known in the art and standard techniques and methodology may be used.

According to this disclosure, a DNA construct comprising nucleic acid encoding a polypeptide having CBHII activity encompassed by this disclosure is constructed to transfer and/or express the variant in a host cell. In one embodiment, the DNA construct is transferred to a host cell by an expression vector which comprises regulatory sequences (e.g. promoters, ribosomal binding sites, transcriptional start and stop sequences, translational start and stop sequences, enhancers, IS activator sequences, cell specific expression sequences, signal sequences, and/or terminators) operably linked to the variant CBH2 coding sequence.

An expression vector comprising a DNA construct with a polynucleotide encoding variant CBHII can be any vector which is capable of replicating autonomously in a given fungal host organism or of integrating into the DNA of the host. In some embodiments, the expression vector is a plasmid or a bacteriophage. In some embodiments, the expression vector is preassembled and contains sequences required for high-level transcription and a selectable marker. In some embodiments, the coding region for variant CBH2 gene or part thereof is inserted into this general-purpose expression vector such that it is under the transcriptional control of the expression construct promoter and terminator sequences. In some embodiments, genes or part thereof are inserted downstream of the strong cbh1 promoter.

Briefly with respect to production are provided in Sambrook et al., (1989) supra, Ausubel (1987) supra, van den Hondel et al. (1991) in Bennett and Lasure (Eds.) MORE GENE MANIPULATIONS IN FUNGI, Academic Press. 396-428 and U.S. Pat. No. 5,874,276. Particularly useful vectors include pTREX, pFB6, pBR322, PUCI8, pUCI00 and pENTR/D. Suitable plasmids for use in bacterial cells include pBR322 and pUC19 permitting replication in *E. coli* and pE194 for example permitting replication in *Bacillus*. Suitable vectors for the expression of the polypeptide having CBHII activity according to the present inventions are pYES2 (Invitrogen), vectors from the pVV-Series, vectors from the pCM-Series, vectors from the pGREG-Series (Jansen et al., Gene 2005 (344) 43-51) vectors from the pMEL-Series (Melcher et al., (2000); Gene 247, 53-61), vectors from the pKM-Series (Melcher et al., (2000); Analytical Biochemistry 277, 109-120) and pYM-Series (Janke et al., Yeast (2004) 21, 947-962). of a C in fungal host cells reference in made to Sambrook et al., (1989) supra, Ausubel (1987) supra, van den Hondel et al. (1991) in Bennett and Lasure (Eds.) MORE GENE MANIPULATIONS IN FUNGI, Academic Press (1991) pp. 70-76 and 396-428; Nunberg et al., (1984) *Mol. Cell Biol.* 4:2306-2315; Boel et al., (1984) 30 *EMBO J.* 3:1581-1585; Finkelstein in BIOTECHNOLOGY OF FILAMENTOUS FUNGI, Finkelstein et al. Eds. Butterworth-Heinemann, Boston, Mass. (1992), Chap. 6; Kinghorn et al. (1992) APPLIED MOLECULAR GENETICS OF FILAMENTOUS FUNGI, Blackie Academic and Professional, Chapman and Hall, London; Kelley et al., (1985) *EMBO J.* 4:475-479; Penttila et al., (1987) *Gene* 61: 155-164; and U.S. Pat. No. 5,874,276. A list of suitable vectors may be found in the Fungal Genetics Stock Center Catalogue of Strains (FGSC, www at fgsc.net). Suitable vectors include those obtained from for example Invitrogen Life Technologies and Promega. Specific vectors suitable for use in fungal host cells include vectors such as pFB6, pBR322, pUC 18, pUC100, pDON™201, pDONR™221, pENTR™, pGEM®3Z and pGEM®4Z.

In some embodiments, the vector can be any vector which, when introduced into a fungal host cell, is integrated into the host cell genome and is replicated. Some non-limiting examples of such vectors is provided in the Fungal Genetics Stock Center Catalogue of Strains (FGSC, <www.fgsc-.net>>), Additional examples of suitable expression and/or integration vectors In some embodiments, nucleic acids encoding variant CBHII encompassed by this disclosure are operably linked to a suitable promoter, which shows transcriptional activity in the host cell. In general, the expression of the variant CBHII is accomplished under any suitable promoter known or later discovered in the art. In some embodiments, the variant CBHII is expressed under a promoter native to the host. In some embodiments, the CBHII variant is expressed under a heterologous promoter that is active in the host cell. For example, if a *Trichoderma* cell is used as the host cell, then advantageously the promoter is active in a *Trichoderma* host cell.

In some embodiments, the promoter is a constitutive or inducible promoter. A "constitutive promoter" is a promoter that is active under most environmental and developmental conditions. An "inducible" or "repressible" promoter is a promoter that is active under environmental or developmental regulation. In some embodiments, promoters are inducible or repressible due to changes in environmental factors including but not limited to, carbon, nitrogen or other nutrient availability, temperature, pH, osmolarity, the presence of heavy metal(s), the concentration of inhibitor(s), stress, or a combination of the foregoing, as is known in the art. In some embodiments, the inducible or repressible promoters are inducible or repressible by metabolic factors, such as the level of certain carbon sources, the level of certain energy sources, the level of certain catabolites, or a combination of the foregoing as is known in the art. In one embodiment, the promoter is one that is native to the host cell. For example, when *T. reesei* is the host, the promoter is a native *T. reesei* promoter such as the cbh1 promoter which is deposited in GenBank under Accession Number D86235.

Suitable non-limiting examples of promoters include cbh1, cbh2, egl1, egl2, egl3, egl4, egl5, xyn1, and xyn2, repressible acid phosphatase gene (phoA) promoter of *P. chrysogenus* (see e.g., Graessle et al., (1997) *Appl. Environ. Microbiol.,* 63:753-756), glucose repressible PCK1 promoter (see e.g., Leuker et al., (1997), *Gene,* 192:235-240), maltoseinducible, glucose-repressible MET3 promoter (see Liu et al., (2006), *Eukary. Cell,* 5:638-649), pKi promoter and cpc1 promoter. Other examples of useful promoters include promoters from *A. awamori* and *A. niger* glucoamylase genes (see e.g., Nunberg et al., (1984) *Mol. Cell Biol.* 15 4:2306-2315 and Boel et al., (1984) *EMBO J.* 3:1581-1585). Also, the promoters of the *T. reesei* xln1 gene may be useful (see e.g., EPA 137280A1).

In some embodiments, the expression vector also includes a transcription termination sequence downstream of the structural gene to provide for efficient termination. In some embodiments, the termination sequence and the promoter sequence are derived from the same source. In other embodiments, the termination sequence is homologous to the host cell. A particularly suitable terminator sequence is cbh1 derived from a *Trichoderma* strain and particularly *T. reesei*. Other useful fungal terminators include the terminator from *A. niger* or *A. awamori* glucoamylase gene (see e.g., Nunberg et al. (1984) supra, and Boel et al., (1984) supra).

The polypeptides produced upon expression of the nucleic acid sequences of this disclosure can be recovered or isolated from the fermentation of cell cultures and substantially purified in a variety of ways according to well established techniques in the art. One of skill in the art is capable of selecting the most appropriate isolation and purification techniques. The CBHII variants of this disclosure can be recovered from culture medium or from host cell lysates. If membrane-bound, it can be released from the membrane using a suitable detergent solution (e.g. Triton-X-100) or by enzymatic cleavage. Cells employed in expression of CBHII can be disrupted by various physical or chemical means, such as freeze-thaw cycling, sonication, mechanical disruption, or cell lysing agents. It may be desired to purify the CBHII from recombinant cell proteins or polypeptides.

The following examples are offered for illustrative purposes only, and are not intended to limit the scope of the present disclosure in any way.

EXAMPLES

In the following examples, materials and methods of the present invention are provided including the determination of catalytic properties of enzymes obtained by the method. It should be understood that these examples are for illustrative purpose only and are not to be construed as limiting this invention in any manner. All publications, patents, and patent applications cited herein are hereby incorporated by reference in their entirety for all purposes.

Example 1

Identification of CBHII Activity as a Key Limiting Activity During Hydrolysis of Biomass Cellobiohydrolyses play a critical role during depolymerisation of cellulose polymers present in a variety of plant or microbial material. These processes require the complementary action of Cellobiohydrolases, Endoglucanases and Beta-Glucosidases.

To determine the most limiting enzyme activity during hydrolysis of a given biomass (e.g. pretreated wheat straw) the concentrations of individual enzymes were varied in synthetic mixtures. Increased CBHII concentrations led to increased overall performances of the whole hydrolysis mixtures. Table 1 summarizes these results:

TABLE 1

| Increase of CBHII concentration in artificial hydrolysis mixtures | Increase of glucose liberation from pretreated wheat straw |
|---|---|
| 3x | 27% |
| 7x | 46% |
| 11x | 73% |

The reactions were started with 20% pretreated wheat straw and run for 18 h at 45° C. Artificial hydrolysis mixtures contained 1 mg/gram dry substance of the commercial enzyme preparation Econase CE (AB Enzymes) and 20 U/gram dry substance of the Beta-Glucosidase Novo 188. Purified CBHII preparations were added in the indicated amounts.

Example 2

Cloning of the *Trichoderma reesei* CBH2 Gene

Chromosomal DNA was isolated from *Trichoderma reesei* strain RutC30 after growth on YPD agar plates (20 g Peptone, 10 g Yeast Extract brought to 1 l with water, stirred, 20 g Agar; $1/10^{th}$ volume of 20% dextrose was added after autoclaving). About 10 mg of biomass was scraped from the plate, combined with 0.2 ml glass beads (0.5 mm diameter) and 500 ml of a 24:24:1 mixture of phenol:chloroform:isoamyl alcohol and vortexed 2-5 min, followed by centrifugation at 10000-15000×g. The supernatant was transferred to a new tube and ethanol precipitated. The pellet was resuspended in 20 ml water. The resulting DNA (2 microliters) was used as template in three PCR reactions using Taq DNA polymerase and containing Primerpairs CBH_01_for (SEQ ID NO 3)/CBH_02_rev (SEQ ID NO 4), CBH_03_for (SEQ ID NO 5)/CBH_04_rev (SEQ ID NO 6) and CBH_05_for (SEQ ID NO 7)/CBH_06_rev (SEQ ID NO 8). The PCRs were run with the following cycling parameters: 94° C., 2 min followed by 25 cycles of 94° C. 1 min, 50° C. 1 min and 72° C. 2 min followed by 5 min at 72° C. The resulting products were purified using the Qiagen MinElute kit and fused within an overlap extension PCR using CBH_01_for (SEQ ID NO 1) and CBH_06_rev (SEQ ID NO 8). The resulting product was ligated into vector pYES2. The DNA sequence of the intron-free CBH II gene was confirmed using a commercial kit (GenomeLab DTCS Quick Start Kit, Beckman Coulter) and the CEQ 2000XL DNA Analysis System (Beckman Coulter).

Example 3

Transformation of *S. cerevisiae* by Lithium Acetate

Frozen stocks (cryostocks) were first generated as follows: A 15 ml preculture of BY4741 was generated in YPD in a 50 ml Erlenmeyer flask incubated at 30° C. and 150 rpm overnight. 10 ml of this culture were used to inoculate 100 ml pre-warmed YPD in a 500 ml Erlenmeyer flask incubated at 30° C. and 150 rpm until an optical density at 600 nm of 6-8 was reached. This culture was mixed with an equal volume of 30% glycerol and stored in 1.6 ml aliquots at −80° C.

Generation of competent cells: 50 ml YPD was inoculated to an initial optical density at 600 nm of 0.5 using cryostocks (above), or using a fresh overnight YPD preculture (above). The 50 ml culture was incubated at 30° C. at 150 rpm 2-4 h until an optical density at 600 nm of 1.0 was reached. The culture was then centrifuged at 1500×g at 20-25° C. for 5 min. The supernatant was discarded and the pellet was resuspended in 20 ml sterile water and centrifuged 5 min at 2500×g. The supernatant was discarded and the pellet resuspended in 1 ml water and transferred to a 2 ml centrifuge tube and re-centrifuged at 10000 to 15000×g for 10 s. The supernatant was discarded and the pellet resuspended and brought to 500 μl with 100 mM lithium acetate (about $2\times10^9$ cells/ml) and incubated 15 min at 30° C.

Transformation of competent cells: Carrier DNA was prepared by boiling 2.63 mg salmon sperm DNA per ml TE buffer (10 mM TrisHCl, 1 mM EDTA, pH 8.0) and stored at −20° C. The plasmid to be transformed (1 μg) was mixed with 38 μl carrier DNA in a 2 ml centrifuge tube and chilled on ice. 50 μl of vortexed competent cells were then mixed with the DNA and 300 μl PEG/LiAc (500 μl of 1 M lithium acetate; 500 μl of water and 4 ml 50% PEG 3350) added and mixed. The mixture was incubated at 30° C. for 30 min, then 42° C. for 20 min and centrifuged at 10000-15000×g for 10 s. The cell pellet was resuspended in 1 ml of YPD and incubated 2 h at 30° C. and 150 rpm, before plating to solid SC-glucose.

Example 4

Screening for and Selection of CBHII Variants with Higher Specific Activity on Solid Matter In order to identify enzyme variants having improved specific activity, a screening approach based on a confocal fluorescence spectroscopy set-up as disclosed in WO94/16313 was used.

A cell suspension of a *Saccharomyces cerevisae* library transformed with plasmids coding for the CBHII variants in culture medium was dispensed at a cfu-concentration ensuring that single cells were dispensed in each well of the micro titer plates. Cultures were grown 72 h at 30° C. and proteins were secreted into the supernatant.

The evaluation of variants with higher specific activity included the measurement of activity on solid substrate (e.g. avicellulose or pretreated wheat straw) and protein quantification by means of ELISA experiments.

Activity on Avicellulose:

One volume of culture supernatant was added to three volumes of a Avicellulose suspension in distilled water (5% dry substance/Fluka) and two volumes of 5 mU/ml beta-Glucosidase (Megazyme) in 200 mM NaAc pH 5.00+0.125% Triton-X-100. The mixture was incubated at 45° C. for at least 2.5 h. After incubation the glucose content was evaluated by adding one volume of Avicellulose-Cellulase-mixture to six volumes assay containing all components for the enzymatic detection of glucose concentrations (Kit from Megazyme). Following the color development for one hour at 37° C. the samples were evaluated by confocal fluorescence spectroscopy.

ELISA:

Supernatants containing CBHII wildtype or variant proteins were added as antigens to a solid phase. The enzymes adsorbed passively during incubation at 37° C. for one hour. After washing and blocking steps (typical ELISA procedures) biotin-labeled antibodies specific for the affinity-tag added to the CBHII wildtype or variant proteins were added and the samples were incubated for one hour at 37° C. Unbound components were washed away leaving the antigen-antibody-complex. During the next step the conjugate, Steptavidin labeled with Peroxidase, was added and incubated for 30 min at 25° C. After the last washing step a chromogene substrate (Amplex Red 5 μM) was added and the reaction was incubated at 25° C. The reaction was terminated after 30 min and the color quantified using a spectrophotometer (ex535 nm/em595 nm).

Compared to the performance of the wildtype protein the variants with improved specific activity yielded a higher fluorescent signal on solid substrates and showed a similar signal during ELISA quantification. They were selected for the generation of further libraries.

Example 5

Acquisition of Specific CBH2 Genes and Determination of DNA and Protein Sequence after Library Screening The screening of a library that contained a diverse population of candidate CBHII enzymes, each individually harboured on the expression plasmid, pYES2, resulted in specific candidates improved in specific activity. Since the individual members of the library were tested as individual cultures, the result of the screening process was the identification of specific cultures that express putatively improved CBH2 genes. The best candidate culture was plated to result in single colonies on solid SC-glucose plates. A resulting isolated colony was inoculated into liquid SC-glucose medium, and plasmid DNA was prepared by Zymoprep kit (Zymo Research). The resulting plasmid DNA was transformed into *E. coli* strain XL1-blue using standard methods, amplified by cell growth in Luria-Bertani solid and liquid medium supplemented with 50 μg/ml ampicillin and isolated by a Qiagen kit. DNA sequencing reactions were generated using the resulting plasmid DNA with a commercial kit (GenomeLab DTCS Quick Start Kit, Beckman Coulter) and the improved CBH2 gene sequence determined using the CEQ 2000XL DNA Analysis System (Beckman Coulter). The DNA sequence of an improved CBH2 gene was unambiguously determined by this method, and the resulting DNA sequence of the CBH2 gene, through application of the standard genetic code for nuclear genes (see Sambrook, J. F; Fritsch, E. F.; Maniatis, T.; Cold Spring Harbor Laboratory Press, Second Edition, 1989, New York), unambiguously determined the amino acid sequence of the encoded CBHII protein.

Example 6

Retransformation and Expression of Specific CBH2 Genes in *Saccharomyces cerevisiae*

After confirmation of the correct DNA sequence, the isolated DNA was transformed into the *Saccharomyces* host strain, BY4741, by the lithium acetate method (see example 3). Transformed cultures were plated to SC-glucose solid medium and incubated at 30° C. Individual colonies were isolated on this solid medium. A resulting isolated colony was inoculated into a 15 ml test tube containing 2 ml SC-glucose which was agitated in a rotary shaker at 150 rpm and 30° C. overnight. From this culture, a 500 ml Erlenmeyer flask containing 100 ml of SC-glucose liquid medium was inoculated to 0.005 OD at 600 nm. The flask was agitated in a rotary shaker at 150 rpm and 30° C. overnight until the optical density at 600 nm was above 2. The culture was subjected to centrifugation and the cell pellet discarded. The improved CBHII protein variants were used and tested as a culture supernatant and/or optionally purified from the supernatant liquid and tested or used as a purified preparation. This process was found scalable to larger volumes

Example 7

Expression and Purification of CBHII Variants

*S. cerevisiae* clones harbouring wildtype or variants of CBH2 were stored as cryo-cultures at −80° C., well known to anyone skilled in the art. A preculture in 3 ml of medium A (16.8 g/l yeast nitrogen base; 2 g/l CSM-URA; 4% galactose; 1% Caseinhydrolysate) supplemented with 100 μg/ml Ampicillin was inoculated from a cryo stock and grown for 48 h at 30° C. in 12 ml tube. These cultures served to incoculate a 1 l expression culture at a density of 100 mOD in Medium A with 100 μg/ml Ampicillin in a 5 l flask. The culture was grown for 72 h at 30° C.

For purification the cells were removed by centrifugation and the supernatant was subjected to a 40-fold concentration by ultra-filtration using a 12 kDa cut-off membrane (Vivaflow 200 module). The purified supernatant was subsequently diafiltrated with the same cut-off to allow a buffer exchange (50 mM $NaH_2PO_4$, 300 mM NaCl, pH 5.0) and concentrated to a final volume of 1/10-1/20 of the original culture volume.

The concentrate was filtered through a 0.45 μm filter and then loaded onto a metal affinity column (Ni-NTA Superflow, Qiagen; bed-volume 15 ml equilibrated with diafiltration buffer). CBHII wildtype and variant proteins were bound via a HIS affinity tag, which was previously added to the proteins. The column was washed with several bed-volumes of diafiltration buffer pH 8.0 followed by five bed-volumes of 4.3% buffer B (buffer B: 50 mM $NaH_2PO_4$, 300 mM NaCl, 250 mM imidazole, pH 8.0). CBHII was eluted five column volumes of 100% buffer B.

Example 8

Improvement of the Specific Activity of the CBHII Variants

Improved variants identified during the screening procedure (described in example 4) were purified as described in example 7 and the protein concentrations were determined using the previously described ELISA method (example 4) and the Bradford method (Methods in Molecular Biology: Vol 149 THE ELISA GUIDEBOOK by John R. Crowther, Human Press Inc., 2001). Protein determinations with both methods led to very similar results indicating the high purity of the protein samples (see table 2). Performances of CBHII wildtype (of *T. reseei*) and variant proteins were evaluated during hydrolysis of avicellulose, pretreated wheat straw or barley glucan and variants showing up to 100% improved specific activity were identified. The improvement factors generated from either protein concentration measurement via Bradford or ELISA were very similar and showed a good correlation. The Genotypes of the improved variants were determined as described in example 5. The positions of the identified CBH II amino acid positions were determined from the CBH II wildtype sequence (see FIG. 2). The following tables summarize the data.

For the determination of specific activity the glucose release activity of the variants was expressed in activity equivalents of the wild-type CBHII enzyme. For this, in each activity determination experiment an appropriate dilution series of the wild-type CBHII enzyme was included. The glucose levels for all variant and wild-type CBHII enzymes were measured. A correlation plot of wild-type CBHII enzyme concentration vs. glucose release was generated.

This correlation was subsequently used to calculate the wild-type CBHII concentrations that are equivalent to the variant enzyme activities.

Specific activity improvement factors of the CBHII variants presented in this document are defined as the following ratio:

$$\frac{\text{activity of the variant enzyme [wild-type CBHII enzyme concentration equivalents]}}{\text{activity of the wild-type enzyme [wild-type CBHII enzyme concentration equivalents]}}$$

TABLE 2

Specific activity improvement factors and genotypes of selected CBHII variants during avicellulose hydrolysis.

| Variant | Improvement factor (Bradford) | Improvement factor (ELISA) | Genotype |
|---|---|---|---|
| Wildtype | 1.00 | 1.00 | — |
| 1-A | 1.17 | 1.00 | Y53Q, S54V |
| 1-B | 1.21 | 1.10 | A65P, A66Y |
| 1-C | 1.12 | 1.12 | Y53A, S54V |
| 1-D | 1.16 | 1.27 | Q37I, N38K |
| 1-E | 1.43 | 1.24 | H438N |
| 1-F | 1.2 | 1.29 | H438S |

TABLE 2-continued

Specific activity improvement factors and genotypes of selected CBHII variants during avicellulose hydrolysis.

| Variant | Improvement factor (Bradford) | Improvement factor (ELISA) | Genotype |
|---|---|---|---|
| 2-A | 1.56 | 1.43 | Y53Q, S54V, H438S |
| 2-B | 1.70 | 1.49 | Y53A, S54V, H438N |
| 2-C | 1.56 | 1.56 | Q37I, N38K, A65P, A66Y, H438S |
| 2-D | 1.65 | 1.87 | Q37I, N38K, Y53A, S54V, A65P, A66Y, H438S |

TABLE 3

Specific activity improvement factors of selected CBHII variants during wheat straw hydrolysis.

| | Improvement factor |
|---|---|
| Variant 1-E | 1.25 |
| Variant 2-B | 1.40 |
| Variant 2-D | 2.00 |

Example 9

Figure 12:
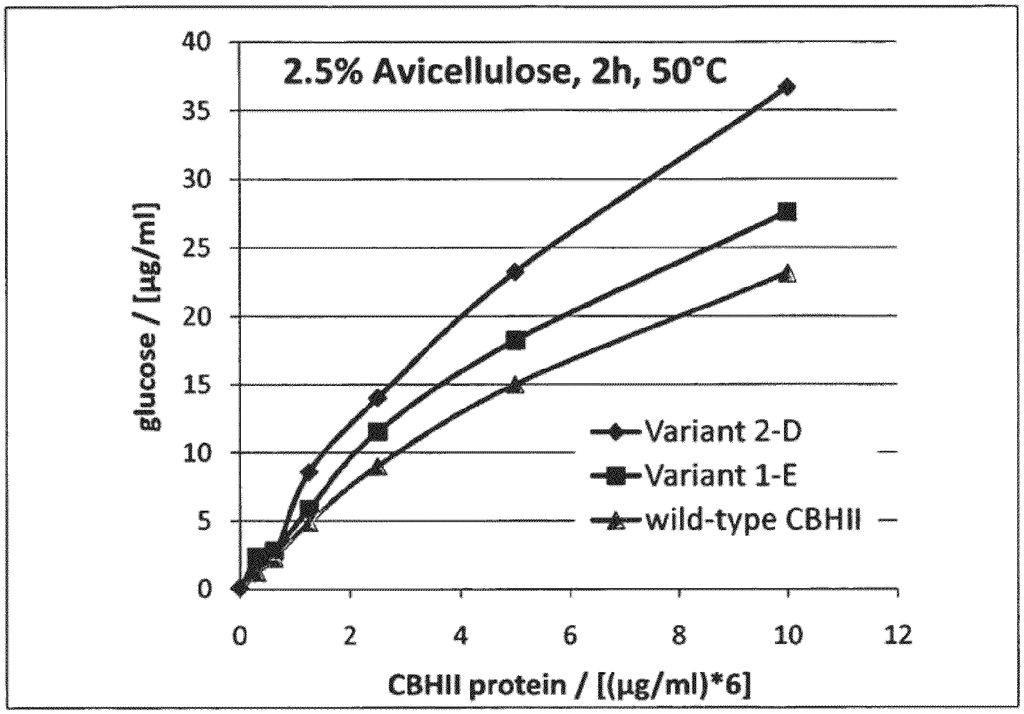
FIG. 12 shows the glucose production upon avicellulose hydrolysis by beta-glucosidase and CBHII wildtype, variant 1-E or variant 2-D proteins.

Identification of CBHII Variants with Improved Specific Activity on Avicellulose CBHII wildtype, variant 1-E and variant 2-D proteins were purified as described in example 7. The protein quantification with Coomassie reagent (Pierce) was performed with a standardized protocol. Pure protein samples (one volume) with concentrations of 0.3125, 0.625, 1.25, 2.5, 5.0 or 10.0 μg/ml and two volumes of 5 mU/ml beta-glucosidase (Megazyme) in 200 mM NaAc pH 5.00+0.125% Triton-X-100 were added to three volumes Avicellulose suspension in distilled water (5% dry substance/Fluka). The mixture was incubated at 50° C. for at least 2.5 h. After this incubation the glucose content was evaluated by adding one volume of the reaction mixture to six volumes assay containing all components for the enzymatic detection of glucose concentrations (Kit from Megazyme). Following the color development of Resazurin to Resorufin (em535 nm/ex595 nm) for one hour at 37° C. the samples were evaluated by confocal fluorescence spectroscopy. The glucose levels reached with the CBHII wildtype, variant 1-E and variant 2-D proteins are shown in FIG. 12.

Figure 6:
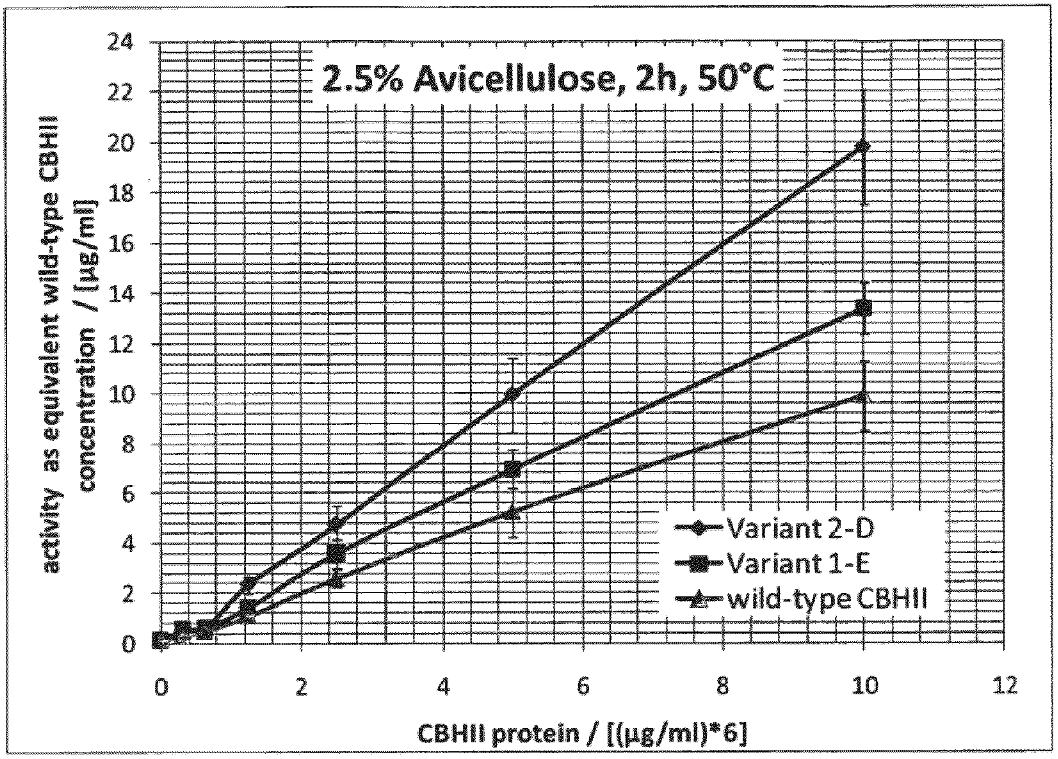
FIG. 6 shows the performance of wild type, variant 1-E and variant 2-D during avicellulose hydrolysis. Equal amounts of each enzyme were tested. Compared to the wildtype CBHII from *Trichoderma reesei*, variant 1-E has up to 1.38× improved specific activity and variant 2-D has up to 2× improved specific activity.

The performance of variants 1-E and 2-D turned out to be significantly improved. As shown in FIG. 6 variant 1-E proteins showed approximately 35% (at 10 g/ml) improved specific activity compared to the wildtype CBHII. At the same protein concentration the specific activity of variant 2-D was approximately 100% improved.

Example 10

Figure 13:
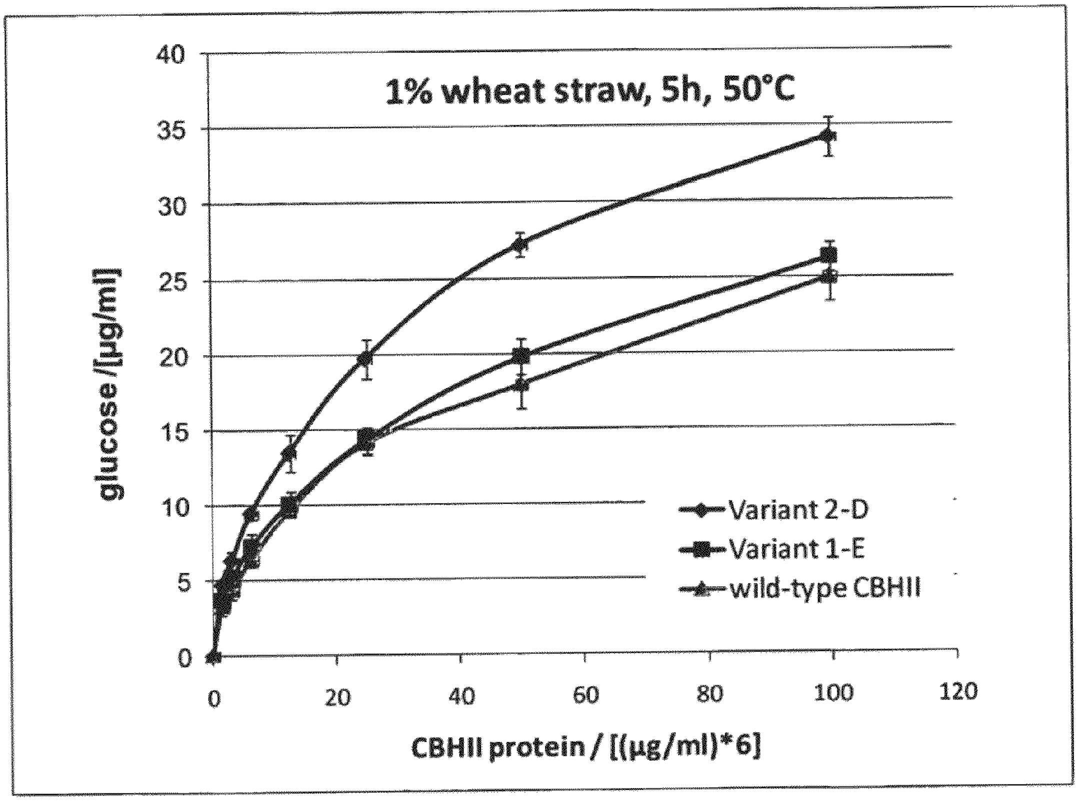
FIG. 13 shows the glucose production upon wheat straw hydrolysis by beta-glucosidase and CBHII wildtype, variant 1-E or variant 2-D proteins.

Identification of CBHII Variants with Improved Specific Activity on Wheat Straw CBHII wild type, variant 1-E and variant 2-D proteins were purified as described in example 7. The protein quantification with Coomassie reagent (Pierce) was performed with a standardized protocol. Pure protein samples (one volume) with concentrations of 1.56, 3.13, 6.25, 12.5, 25, 50 or 100 μg/ml and two volumes of 200 mU/ml beta-glucosidase (Megazyme) in 200 mM NaAc pH 5.00+0.125% Triton-X-100 were added to three volumes wheat straw suspension in distilled water (2% dry substance). The mixture was incubated at 50° C. for at least 2.5 h. After incubation the glucose content was evaluated by adding one volume of the reaction mix to six volumes assay containing all components for the enzymatic detection of glucose concentrations (Kit from Megazyme). Following the color development of Resazurin to Resorufin (em535 nm/ex595 nm) for one hour at 37° C. the samples were evaluated by confocal fluorescence spectroscopy. The glucose levels reached with the CBHII wildtype, variant 1-E and variant 2-D proteins are shown in FIG. 13.

Figure 8:
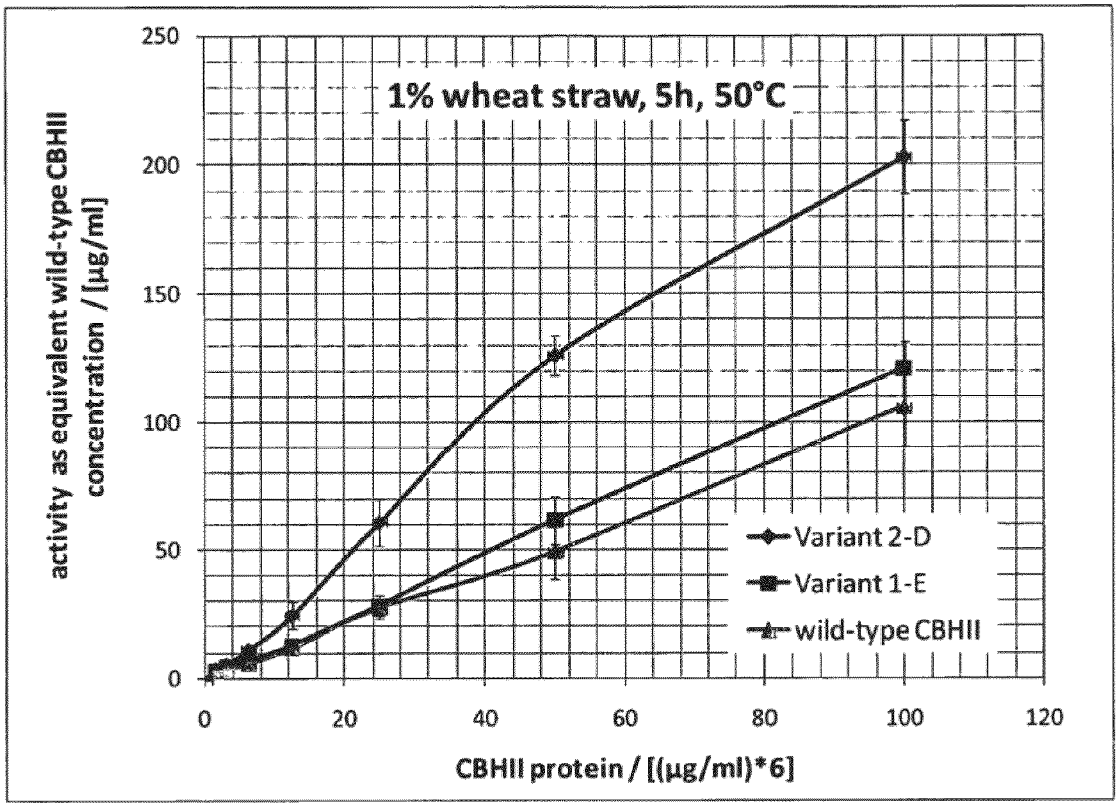
FIG. 8 shows the performance of wild type CBHII from *Trichoderma reesei*, variant 1-E and variant 2-D during wheat straw hydrolysis. Equal amounts of each enzyme were tested. Compared to the wild type, variant 1-E has up to 1.2× improved specific activity and variant 2-D has up to 2× improved specific activity.

As shown in FIG. 8 variant 1-E proteins showed approximately 23% (at 50 g/ml) improved specific activity compared to the wildtype CBHII. At the same protein concentration the specific activity of variant 2-D was approximately 112% improved.

Example 11

Figure 14:
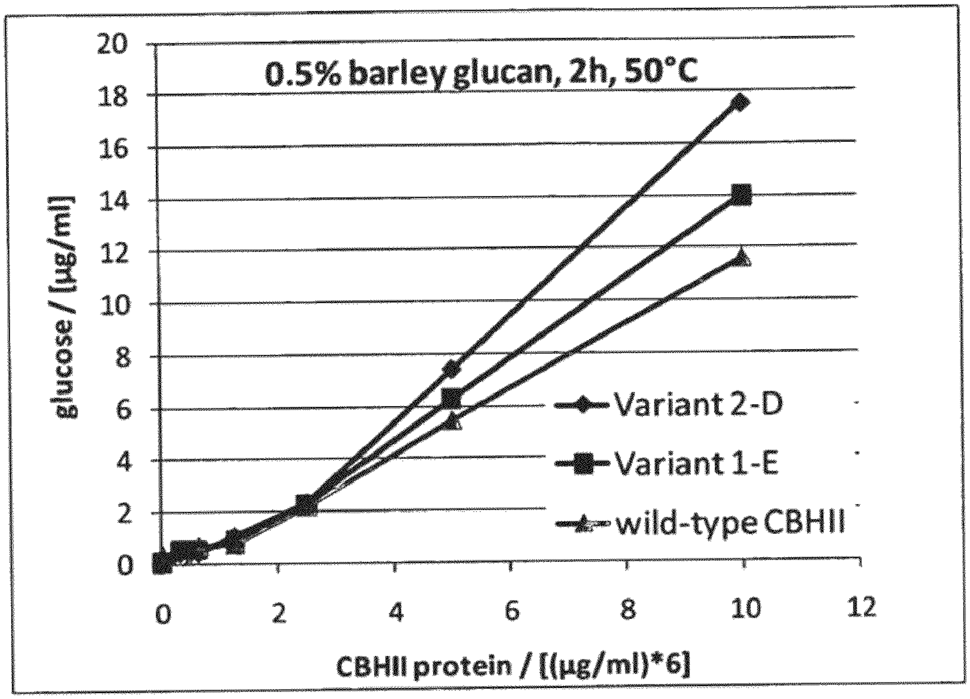
FIG. 14 shows the glucose production upon barley glucan hydrolysis by beta-glucosidase and CBHII wildtype, variant 1-E or variant 2-D proteins.

Identification of CBH II Variants with Improved Specific Activity on Barley Glucan CBH II wildtype, variant 1-E and variant 2-D proteins were purified as described in example 7. The protein quantification with Coomassie reagent (Pierce) was performed with a standardized protocol. Pure protein samples (one volume) with concentrations of 0.3125, 0.625, 1.25, 2.5, 5.0 or 10.0 μg/ml and two volumes of 50 mU/ml beta-Glucosidase (Megazyme) in 200 mM NaAc pH 5.00+0.125% Triton-X-100 were added to three volumes Barley Glucan solution in distilled water (1% w/v; Megazyme). The mixture was incubated at 50° C. for at least 2 h. After incubation the glucose content was evaluated by adding one volume of the reaction mixture to six volumes assay containing all components for the enzymatic detection of glucose concentrations (Kit from Megazyme). Following the color development of Resazurin to Resorufin (em535 nm/ex595 nm) for one hour at 37° C. the samples were evaluated by confocal fluorescence spectroscopy. The glucose levels reached with the CBHII wildtype, variant 1-E and variant 2-D proteins are shown in FIG. 14.

Figure 9:
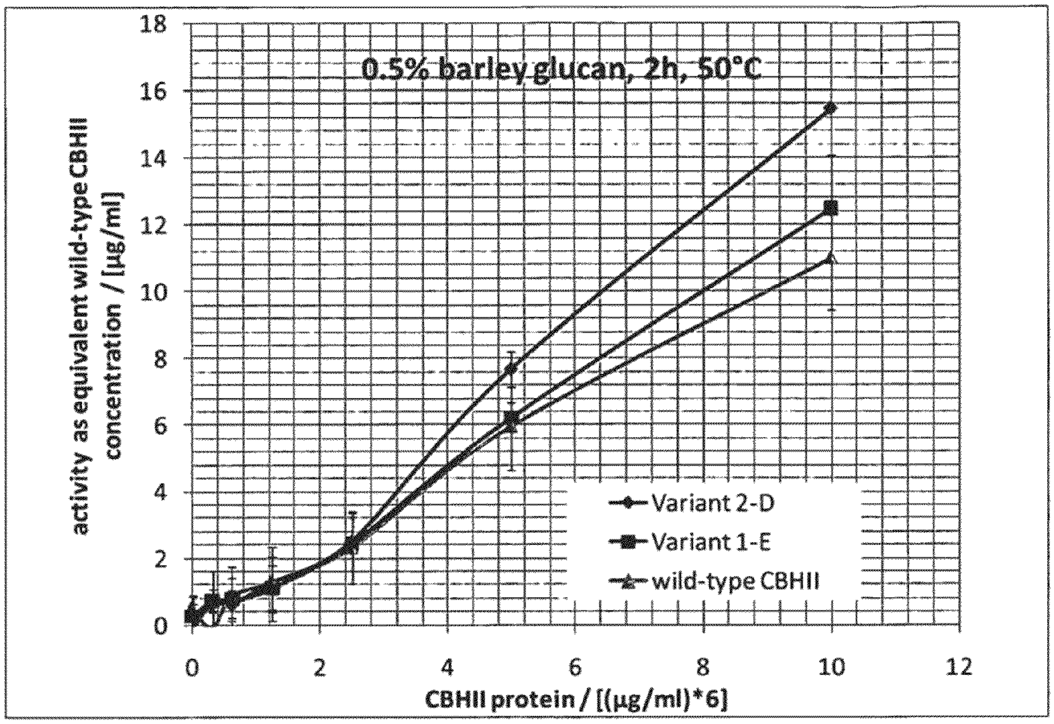
FIG. 9 shows the performance of wildtype CBHII from *Trichoderma reesei*, variant 1-E and variant 2-D during barley glucan hydrolysis. Equal amounts of each enzyme were tested. Compared to the wildtype variant 1-E has an improved specific activity and variant 2-D has also an improved specific activity.

As shown in FIG. 9 variant 1-E proteins has improved specific activity compared to the wildtype CBHII. At the same protein concentration the specific activity of variant 2-D was also improved.

The invention claimed is:

1. A polypeptide having cellobiohydrolase II activity, wherein said polypeptide comprises a substitution or deletion at a position corresponding to residue H438 in CBHII from *Trichoderma reesei* (SEQ ID NO: 1), or a polypeptide at least 75% identical to SEQ ID NO: 1.

2. The polypeptide of claim 1, wherein said polypeptide comprises a substitution at a position corresponding to residue H438S or H438N.

3. The polypeptide of claim 2, wherein said polypeptide comprises substitutions at positions corresponding to residues selected from the group consisting of:

a) H438S
b) H438N
c) Y53A, S54V, H438N
d) Y53Q, S54V, H438S
e) Q37I, N38K, A65P, A66Y, H438S
f) Q37I, N38K, Y53A, S54V, A65P, A66Y and H438S.

4. A polypeptide having cellobiohydrolase II activity, said polypeptide having an amino acid sequence that varies from the amino acid sequence of the wild type CBHII from *Trichoderma reesei* (SEQ ID NO: 1)), wherein the amino acid sequence of the polypeptide comprises at least one variation as compared with SEQ ID NO: 1, and wherein the variation occurs at position 438 of SEQ ID NO: 1, and wherein the variation can comprise a substitution or deletion.

5. The polypeptide of claim 4, wherein the polypeptide further comprises a variation of one, two, three, four, five, or six positions selected from the group consisting of: Q37, N38, Y53, S54, A65, and A66.

6. The polypeptide of claim 5, wherein the polypeptide comprises a variation at position H438S and a variation selected from the group consisting of Q37I, N38K, Y53A, S54V, A65P, and A66Y.

7. A polypeptide of claim 5, wherein said polypeptide of the substitutions selected from the group consisting of:

a) H438S
b) H438N
c) Y53A, S54V, H438N
d) Y53Q, S54V, H438S
e) Q37I, N38K, A65P, A66Y, H438S
f) Q37I, N38K, Y53A, S54V, A65P, A66Y and H438S.

8. A polypeptide which has at least a minimum percent sequence identity and/or percent homology to the polypeptide of claim 1, wherein the minimum percent identity and/or homology is at least 80%.

9. A nucleic acid encoding a polypeptide of claim 1.

10. A host cell comprising the nucleic acid of claim 9.

11. An enzyme composition comprising at least one polypeptide of claim 1.

12. A method of producing a polypeptide having cellobiohydrolase II activity comprising the steps of: (a) culturing the host cell of claim 10 in a suitable culture medium under suitable conditions to produce polypeptide having cellobiohydrolase II activity; (b) isolate said produced polypeptide.

13. A feed additive comprising at least one polypeptide of claim 1.

14. A method of converting biomass to sugars comprising contacting said biomass with at least one polypeptide of claim 1.

15. A method of alcohol fermentation comprising the use of at least one polypeptide of claim 1.

16. A polypeptide which has at least a minimum percent sequence identity and/or percent homology to the polypeptide of claim 1, wherein the minimum percent identity and/or homology is at least 85%.

17. A polypeptide which has at least a minimum percent sequence identity and/or percent homology to the polypeptide of claim 1, wherein the minimum percent identity and/or homology is at least 90%.

18. A polypeptide which has at least a minimum percent sequence identity and/or percent homology to the polypeptide of claim 1, wherein the minimum percent identity and/or homology is at least 95%.

19. A polypeptide which has at least a minimum percent sequence identity and/or percent homology to the polypeptide of claim 1, wherein the minimum percent identity and/or homology is at least 97%.

20. A polypeptide which has at least a minimum percent sequence identity and/or percent homology to the polypeptide of claim 1, wherein the minimum percent identity and/or homology is at least 99%.

* * * * *